US005733933A

United States Patent [19]
Bucala et al.

[11] Patent Number: 5,733,933
[45] Date of Patent: Mar. 31, 1998

[54] METHODS AND MATERIALS FOR THE DIAGNOSIS AND TREATMENT OF CONDITIONS SUCH AS STROKE

[75] Inventors: Richard J. Bucala, New York; Helen Vlassara; Anthony Cerami, both of Shelter Island, all of N.Y.; Kevin J. Tracey, Old Greenwich, Conn.

[73] Assignee: The Picower Institute for Medical Research, Manhasset, N.Y.

[21] Appl. No.: 473,009

[22] Filed: Jun. 7, 1995

Related U.S. Application Data

[63] Continuation-in-part of Ser. No. 418,525, Apr. 7, 1995, which is a continuation-in-part of Ser. No. 319,747, Oct. 7, 1994, which is a continuation-in-part of Ser. No. 29,417, Mar. 11, 1993, and Ser. No. 236,228, Apr. 29, 1994, Pat. No. 5,468,777, which is a continuation-in-part of Ser. No. 825,598, Jan. 27, 1992, Pat. No. 5,334,617, which is a continuation-in-part of Ser. No. 805,200, Dec. 10, 1991, Pat. No. 5,238,968, which is a division of Ser. No. 481,869, Feb. 20, 1990, Pat. No. 5,128,360, which is a continuation-in-part of Ser. No. 220,504, Jul. 18, 1988, abandoned, which is a division of Ser. No. 798,032, Nov. 14, 1985, Pat. No. 4,758,583, which is a continuation-in-part of Ser. No. 590,820, Mar. 19, 1984, Pat. No. 4,665,192, said Ser. No. 29,417, is a continuation-in-part of Ser. No. 887,279, May 21, 1992, abandoned.

[51] Int. Cl.$^6$ ................................................ A61K 31/155
[52] U.S. Cl. .................................................. 514/634
[58] Field of Search .............................. 424/9.2; 514/634

[56] References Cited

U.S. PATENT DOCUMENTS

| | | |
|---|---|---|
| 4,778,752 | 10/1988 | Curtiss et al. |
| 4,900,747 | 2/1990 | Vlassara et al. |
| 4,983,604 | 1/1991 | Ulrich et al. |
| 5,100,919 | 3/1992 | Urich et al. |
| 5,106,877 | 4/1992 | Ulrich et al. |
| 5,238,963 | 8/1993 | Cerami et al. |
| 5,246,970 | 9/1993 | Williamson et al. |
| 5,246,971 | 9/1993 | Williamson et al. |
| 5,273,875 | 12/1993 | Griffith . |
| 5,358,969 | 10/1994 | Williamson et al. |
| 5,403,861 | 4/1995 | Goldin et al. ............... 514/634 |
| 5,430,039 | 7/1995 | Roberts-Lewis et al. |

FOREIGN PATENT DOCUMENTS

| | | |
|---|---|---|
| 0 096439 A3 | 12/1983 | European Pat. Off. |
| 0 222313 A2 | 4/1987 | European Pat. Off. |
| WO 85/04169 | 9/1985 | WIPO . |
| WO 93/04086 | 3/1993 | WIPO . |

OTHER PUBLICATIONS

Vlassara et al., "Function of Macrophage Receptor for Nonenzymatically Glycosylated Proteins is Modulated by Insulin Levels", Diabetes, 35(1), p. 11a (1986).

Vlassara et al., "Accumlation Of Diabetic Rat Peripheral Nerve Myelin by Macrophaghes Increases With the Presence of Advanced Glycosylation Endproducts", J. Exp. Med., 160, pp. 197–207 (1984).

Vlassara et al., "Recognition and Uptake of Human Diabetic Peripheral Nerve Myelin by Macrophages", Diabetes, 34 No. 6, pp. 553–557 (1985).

Vlassara et al., "High–Affinity Receptor–Mediated Uptake and Degradation of Glucose–Modified Proteins: A Potential Mechanism for the Removal of Senescent Macromoleules", Proc. Natl. Acad. Sci. U.S.A., 82, pp. 5588–5592 (1985).

Vlassara et al., "Novel Macrophage Receptor for Glucose–Modified Proteins is Distinct From Previously Described Scavenger Receptors", J. Exp. Med., 164, pp. 1301–1309 (1986).

Cerami, A. et al., "Role of Nonenzymatic Glycosylation in Atherogenesis", Journal of Cellular Biochemistry, 30, pp. 111–120 (1986).

Radoff, S. et al., "Characterization of a Solubilized Cell Surface Binding Protein on Macrophages Specific for Proteins Modified Nonenzymatically by Advanced Glycosylation End Products", Arch. Biochem. Biophys., 263 No. 2, pp. 418–423 (1988).

Radoff, S. et al., "Isolation of a Surface Binding Protein Specific for Advanced Glycosylation End Products from the Mouse Macrophage–Derived Cell Line Raw 264.7", Diabetes, 39, pp. 1510–1518 (1990).

Yang, Z. et al., "Two Novel Rat Liver Membrane Proteins That Bind Advanced Glycosylation Endproducts: Relationship to Macrophage Receptor for Glucose–Modified Proteins", J. Exp. Med., 174, pp. 515–524 (1991).

Witztum, J.L., and D. Steinberg, "Role of oxidized low density lipoprotein in atherogenesis", J. Clin. Invest. 88, pp. 1785–1792 (1991).

Goldstein, J.L., Y.K. Ho, S.K. Basu, and M.S. Brown, "Binding site on macrophages that mediates uptake and degradation of acetylated low density lipoprotein, producing massive cholesterol deposition", Proc. Natl. Acad. Sci. USA, 76, pp. 333–357 (1979).

(List continued on next page.)

*Primary Examiner*—Brian M. Burn
*Attorney, Agent, or Firm*—Klauber & Jackson

[57] ABSTRACT

The in vivo oxidation of lipids and lipid-containing molecules has been discovered to be initiated by the concurrent reaction of such lipid materials with reducing sugars such as glucose, advanced glycosylation endproducts such as AGE-peptides, or a compound which forms advanced glycosylation endproducts, to form materials or particles known as AGE-lipids. AGE-lipids have been implicated in the aging process, the abnormal formation of lipofuscin and in various disease states such as diabetes, atherosclerosis, and stroke. Methods of treating stroke, and especially inhibiting the infarct size of stroke, using agents which inhibit the formation of AGE-lipids are disclosed. Additionally, a method of screening for neuroprotective agents which can be used to reduce the size and severity of the infarct size is disclosed.

2 Claims, 7 Drawing Sheets

OTHER PUBLICATIONS

Fogelman, A.M. J.S. Schecter, M. Hokom, J.S. Child, and P.A. Edwards, "Malodialdehyde alteration of low density lipoprotein leads to cholesterol accumulation in human monocyte-macrophages", Proc. Natl. Acad. Sci. USA, 77, pp. 2214–2218 (1980).

Sparrow, C.P., S. Parthasarathy, and D. Steinberg, "A macrophage receptor tht recognizes oxidized LDL but not acetylated LDL", J. Biol. Chem., 264 pp. 2599–2604 (1989).

Ross, R. "The pathogenesis of atherosclerosis", An update. New Eng. J. Med., 314, pp. 488–500 (1986).

Quinn, M.T., S. Pathasarathy, L.G. Fong, and D. Steinberg, "Oxidatively modified low density lipoprotein: a potential role in recruitment and retention of monocyte/macrophages during atherogensis", Proc. Natl. Sci. USA, 84, pp. 2095–2998 (1987).

Hessler, J.R., D.W. Morel, L.J. Lewis and G.M. Chisolm, "Lipoprotein oxidation and lipoprotein–induced cytotoxicity", Arteriosclerosis, 3, pp. 215–222 (1983).

Kugiyama, K., S.A. Kerns, J.D. Morrisett, R. Roberts, and P.D. Henry, "Impairment of endothelium–dependent arterial relaxation by lysolecithin in modified low–density lipoproteins", Nature, 344, pp. 160–162 (1990).

Rajavashiesth, T.B., A. Andalibi, M.C. Territo, J.A. Berliner, M. Navab, A.M. Fogelman, and A.J. Lusis, "Induction of endthelial cell expression of granulocyte and macrophage colony–stimulating factors by modified low–density lipoproteins. Nature, 344, pp. 254–257 (1990).

Cushing, S.D., J.A. Berliner, A.J. Valente, M. Navab, F. Parhami, R. Gerrity, C.J. Schwartz, and A.M. Fogelman, "Minimally modified low density lipoprotein induces monocyte chemotactic protein 1 in human endothelial cells and smooth muscle cells", Proc. Natl. Acad. Sci. USA, 87, pp. 5134–5138 (1990).

Kita, T., Y. Nagano, M. Yokode, K. Ishii, N. Kume, A. Ooshima, H. Yoshida, and C. Kawai. "Probucol prevents the progression of atherosclerosis in Watanabe heritable hyperlipidemic rabbit, an animal mode for familial; hypercholesterolemia", Proc. Natl. Acad. Sci. USA, 84, pp. 5928–5931 (1987).

Esterbauer, H.G. Jürgens, O. Quehenberger, and Koller, E. "Autoxidation of human low density lipoprotein: loss of polyunsaturated fatty acids and vitamin E and generation of aldehydes", J. Lipid Res. . 28, pp. 505–509 (1987).

Quehenberger, O., E. Koller, G. Jürgens, and H. Esterbauer, "Investigation of lipid peroxidation in human low density lipoprotein", Free Radical Res. Commun. 3, pp. 233–242 (1987).

Steinbrecher, U.P. "Oxidation of human low density lipoprotein results in derivitization of lysine residues of apolipoprotein B by lipid peroxide decomposition products", J. Biol. Chem., 262, pp. 3603–3608 (1987).

Steinbrecher, U.P., S. Parthasarathy, D.S. Leake, J.L. Witztum, and D. Steinberg, "Modification of low density lipoprotein by endothelial cells involves lipid peroxidation and degradation of low density lipoprotein phospholipids", Proc. Natl. Acad. Sci. USA, 81, pp. 3883–3887 (1984).

Parthasarathy, S., E. Wieland, and D. Steinberg, "A role for endothelial cell lipoxygenase in the oxidative modifications of low density lipoprotein", Proc. Natl. Acad. Sci. USA, 86, pp. 1046–1050 (1989).

Klaassen, C.D. "Heavy metals and heavy metal antagonists, in Goodman and Gilman's The Pharmacological Basis of Therapeutics. A.G. Gilman, L.S. Goodman, T.W. Rall and F. Murad. Macmillan, New York, pp. 1592–1614 (1985).

Frei, B., Y. Yamamoto, D.Niclas, and B.N. Ames. "Evaluation of an isolumino chemiluminescence assay for the detection of hydroperoxides in human blood plasma", Anal. Biochem., 175, pp. 120–130 (1988).

Frei, B., R. Stocker, and B.N. Ames, "Antioxidant defenses and lipid peroxidation in human blood plasma", Proc. Natl. Acad. Sci. USA, 85, pp. 9748–9752 (1988).

Bucala, R., and Cerami, "Advanced glycosylation: chemistry, biology, and implications for diabetes and aging", Adv. Pharmacol. 23, pp. 1–34 (1992).

Njoroge, F.G. and V.M. Monnier, "The chemistry of the Maillard reaction under physiological conditions: A review", Prog. Clin. Biol. Res., 304, pp. 85–107 (1989).

Brownlee, M., A. Cerami, and H. Vlassara, "Advanced glycosylation endproducts in tissue and the biochemical basis of diabetic complications", N. Eng. J. Med., 318, pp. 1315–1321 (1988).

Monnier, V.M., R.R. Kohn, and A. Cerami, "Accelerated age–related browning of human collagen in diabetes mellitus", Proc. Natl. Acad. Sci. USA, 81, pp. 583–587 (1984).

Bucala, R., K.J. Tracey, and A. Cerami, "Advanced glycosylation products quench nitric oxide and mediate defective endothelium—dependent vasodilatation in experminental diabetes", J. Clin. Invest., 87, pp. 432–438 (1991).

Esposito, C., H. Gerlach, J. Brett, D. Stern, and H. Vlassara, "Endothelial receptor–mediated binding of glucose–modified albumin is associated with increased monolayer permeability and modulation of cell surface coagulant properties", J. Exp. Med., 170, pp. 1387–1407 (1989).

Vlassara, H., M.Brownlee, K.R. Manogue, C.A. Dinarello, and A. Pasagian, "Cachectin/TNF and IL–1 induced by glucose–modified proteins: Role in normal tissue remodeling", Science, 240, pp. 1546–1548 (1988).

Jain, S.K., R. McVie, J. Duett, and J.J. Herbst, "Erythrocyte membrane lipid peroxidation and gylcosylated hemoglobin in diabetes", Diabetes, 38, pp. 1539–1543 (1989).

Nishigaki, I., M. Hagihara, H. Tsunekawa, M. Maseki, and K. Yagi, "Lipid peroxide levels of serum lipoprotein fractions of diabetic patients", Biochem. Med., 25, pp. 373–378 (1981).

Armstrong, D.N. Abdella, A. Salman, N. Miller, E.A. Rahman, and M. Bojancyzk, "Relationship of lipid peroxides to diabetic complications", J. Diabetes Complications, 6, pp. 116–122 (1992).

London, E., and G.W. Feigenson, "A convenient and sensitive fluorescence assay for phospholipid vesicles using diphenylhexatriene, Anal. Biochem. 88, pp. 203–211 (1978).

Jain, S.K., and D. Subrahmanyn, "Two demensional thinlayer chromatography of polar lipids", Ital. J. Biochem., 27, pp. 11–18 (1978).

Havel, R.J., H.A. Eder, and J.H. Bragdon, "Distribution and chemical composition of ultracentrifugally seperat4ed lipoproteins in human serum", J. Clin. Invest., 34, pp. 1345–1353 (1955).

Lowry, O., N.J. Rosebrough, A.L. Farr, and R.J. Randall, "Protein measurement with Folin phenol reagent", J. Biol. Chem. 193, pp. 265–275 (1951).

Makita, Z., H. Vlassara, A. Cerami and R. Bucala, "Immunochemical detection of advanced glycosylation end products in vivo", J. Biol. Chem. 267, pp. 5133–5138 (1992).

Makita, Z., H. Vlassara, E. Rayfield, K. Cartwright, E. Friedman, R. Rouby, A. Cerami, and R. Bucala, "Hemoglobin–AGE: A circulating marker of advanced glycosylation", Science, 258, pp. 651–653 (1992).

Kikugawa, K., T. Kojima, S. Yamaki, and H. Kosugi, "Interpretation of the thiobarituric acid reactivity of rat liver and brain homogenates in the presence of ferric ion and ethylenediaminetertraacetic acid", Anal. Biochem., 202, pp. 249–255 (1992).

Ohkawa, H., N. Ohishi, and K. Yagi, "Assay for lipid peroxides in animal tissues by thiobarbituric acid reaction", Anal. Biochem., 95, pp. 351–358 (1979).

Chen, H.–J. C., and A. Cerami, "Mechanism of inhibition of advanced glycosylation by aminoguanidine in vitro", J. Carbohydate Chem. (In press).

Picard, S., S. Parthasarathy, J. Fruebis, and J.L. Witztum, "Aminoguanidine inhibits oxidative modification of low density lipoprotein and the subsequent increase in uptake by macrophage scavenger receptors", Proc. Natl. Acad. Sci. USA, 89, pp. 6876–6880 (1992).

Hicks, M., L. Delbridge, D.K. Yue, and T.S. Reeve, "Catalysis of lipid peroxidation by glucosse and glycosylated collagen", Biochem. Biophys. Res. Commun. 151, pp. 649–655 (1988).

Mullarkey, C.J., D. Edelstein, and M. Brownlee, "Free radical generation by early glycation products: A mechanism for accelerated atherogenesis in diabetes", Biochem. Biophys. Res. Commun., 173, pp. 932–939 (1990).

Pongor, S., P.C. Ulrich, F.A. Bencsath, and A. Cerami, "Aging of proteins: isolation and identification of a fluorescent chromophore from the reactioin of polypeptides with glucose", Proc. Natl. Acad. Sci. USA, 81, pp. 2684–2688 (1984).

Ahmed, M. U., J.A. Dunn, M.D. Walla, S.R. Thorpe, and J.W. Baynes, "Oxidative degradation of glucose adducts to protein", J. Biol. Chem., 263, pp. 8816–8821 (1988).

Grandhee, S.K., and V.M. Monnier, "Mechanism of formation of the Maillard protein cross–link pentosidine, Glucose, fructose, and ascorbate as pentosidine precursors", J. Biol. Chem., 266, pp. 11649–11653 (1991).

Namiki, M., and T. Hayashi, "Formation of novel free radical product in an early stage of Maillard reaction", Prog. Fd. Nutr. Sci., 5, pp. 81–91 (1981).

Tsuchida, M., T. Miura, and K. Aibara, "Lipofuscin and lipofuscin–like substances", Chem. Phys. Lipids, 44, pp. 297–325 (1987).

T. Soulis–Liparota, M. Cooper, D. Papazoglou, B. Clarke, and G. Jerums, "Retardation by aminoguanidine of development of albuminuria, mesangial expansion, and tissue fluorescence in streptozotocin–induced diabetic rat", Diabetes, 40, pp. 1328–1334 (1991).

Hammes, H.P., S. Martin, K. Federlin, K. Geisen, and M. Brownlee, "Aminoguanidine treatment inhibits the development of experimental diabetic retinopathy", Proc. Natl. Acad. Sci. USA, 88, pp. 11555–11558 (1991).

Yagishashi, S., M. Kamijo, M. Baba, N. Yagihashi, and K. Nagai, "Effect of aminoguandine on functional and structrual abnormalities in peripheral nerve of STZ–induced diabetic rats," Diabetes, 44, pp. 47–52 (1992).

O'Brein, R.C., S. Panagiotopoulos, M.E. Cooper and G. Jerums, "Anti–atherogenic effect of aminoguanidine, and inhibitor of advanced glycation", Diabetes, 41 (Suppl 1) 16A (1992).

Babiy, Alexander V. et al., Biochemical Pharmol., 43(1):995–1001 (1992).

Sakurai, Tamiko et al., Biochemical and Biophysical Research Communications, 177(1):433–439 (1991).

Duell P. Barton, et al., Diabeties, 39:1257–1263 (1990).

Calvo, C. et al., Diabete & Metabolisme (Paris), 14:264–269 (1988).

Brownlee et al., 1985, Diabetes, 34:938–941.

Ponsin et al., 1991, Diabete & Metbolisme, 17:497–502.

Pescarmona, 1987, Diabetologia, 30:568A.

Kirstein et al., 1990, Proc. Natl. Acad. Sci. USA, 87:9010–14.

Corbett et al., 1993, Autoimmunity 15:145–153.

Corbett et al., 1992, Biochemical J. 287:229–235.

Griffiths et al., 1993, Br. J. Pharmacol. 110:963–968.

Williamson et al., 1990, Diabetes and Metabolism 16:369–370.

CONTROL                    AGE

METHODS AND MATERIALS FOR THE DIAGNOSIS AND TREATMENT OF CONDITIONS SUCH AS STROKE

CROSS-REFERENCE TO RELATED APPLICATION

The present application is a Continuation-in-Part of application Ser. No. 08/418,525, filed Apr. 7, 1995, which is a Continuation-In-Part of application Ser. No. 08/319,747, filed Oct. 7, 1994, which is a Continuation-in-Part of application Ser. No. 08/236,228, filed Apr. 29, 1994 (now U.S. Pat. No. 5,462,777); said Ser. No. 08/236,228 being a Continuation-In-Part of U.S. application Ser. No. 07/825, 598, filed Jan. 27, 1992, now U.S. Pat. No. 5,334,617, which is a Continuation-In-Part of application Ser. No. 07/805,200, filed Dec. 10, 1991, now U.S. Pat. No. 5,238,968; which is a Division of application Ser. No. 07/481,869, filed Feb. 20, 1990, now U.S. Pat. No. 5,128,360; which is a Continuation-in-Part of application Ser. No. 07/220,504, filed Jul. 18, 1988, now abandoned; which is a Division of application Ser. No. 06/798,032, filed Nov. 14, 1985, now U.S. Pat. No. 4,758,583, which is a Continuation-in-Part of application Ser. No. 06/590,820, filed Mar. 19, 1984, now U.S. Pat. No. 4,665,192; and said Ser. No. 08/319,747 being a Continuation-in-Part of application Ser. No. 08/029,417, filed Mar. 11, 1993, which is in turn, a Continuation-In-Part of application Ser. No. 07/887,279, filed May 21, 1992 now abandoned, both by certain of the inventors herein. Priority is claimed under 35 U.S.C. §120 as to the earlier filed applications, and the disclosures thereof are incorporated herein by reference.

This invention was made with partial assistance from grant Nos. AGO-9453, AGO-6943 and DK 19655-15 from the National Institutes of Health. The government may have certain rights in this invention.

RELATED PUBLICATIONS

The Applicants are co-authors of the following articles directed to the subject matter of the present invention: Bucala, R., et al., (1993) "Lipid Advanced Glycosylation: Pathway for Lipid Oxidation In Vivo, P.N.A.S. USA, 90:6434–6438.

TECHNICAL FIELD OF THE INVENTION

The present invention relates generally to the non-enzymatic glycosylation of proteins and other biomolecules and the often consequent formation of advanced glycosylation endproducts (AGEs), and particularly to the formation of lipid-AGEs and the role that glycosylated lipids and lipoproteins may play as markers and actors in conditions such as atherosclerosis and diabetes. The instant invention also relates particularly to the treatment of stroke, and the reduction of size and severity of the infarct size resultant therefrom.

BACKGROUND OF THE INVENTION

Glucose and other reducing sugars attach non-enzymatically to the amino groups of proteins in a concentration-dependent manner. Over time, these initial Amadori adducts undergo further rearrangements, dehydrations and cross-linking with other proteins to accumulate as a family of complex structures which are referred to as Advanced Glycosylation Endproducts (AGEs). Beginning with the early work of the present applicants and extending to the present, substantial progress has been made toward the elucidation of the role and clinical significance of advanced glycosylation endproducts, so that it is now acknowledged that many of the conditions heretofore attributed to the aging process or to the pathological effects of diseases such as diabetes, are attributable at least in part to the formation of AGEs in vivo.

Advanced glycosylation tends to occur on molecules with long half-lives, under conditions of relatively high sugar concentration, such as in diabetes mellitus. Numerous studies have suggested that AGEs play an important role in the structural and functional alteration which occurs during aging and in chronic disease. Additionally, advanced glycosylation endproducts are noted to form more rapidly in diabetic and other diseased tissue than in normal tissue.

A particular area that has received attention in light of the series of discoveries regarding the relationship of advanced glycosylation of proteins to the etiology of conditions such as diabetes and aging, has been the set of events that coincide in the development of vascular disease. Specifically, the formation of atherosclerotic lesions and plaques is an example of a condition that has been extensively investigated with a view to elucidating the interrelationship, if any, that exists between the oxidation of low density lipoproteins (LDL) and the presence and formation of AGEs.

In this connection, research connected with the phenomenon of protein glycosylation has been extended in scope to a broad variety of biological molecules in an effort to first identify the existence of AGE formation in these diverse compartments, and thereafter, to determine the significance, if any, that may be attributable thereto. It is in this context that the discovery of a reaction of this type involving lipids as defined later on herein (e.g., the formation of AGE-lipids), was initially presented in parent application Ser. No. 07/887,279 (filed May 21, 1992) (now abandoned), referred to hereinabove and incorporated herein.

The formation and existence of AGE-lipids was postulated and observed in the said parent application, and the significance of these materials as markers and actors in the conditions already associated with the presence of AGEs, was likewise noted. As stated therein, AGE-lipids are important biologically. The formation of AGEs on lipids has been observed to begin the lipid oxidation process and thus may render these species more active biologically and chemically, and in particular, more prone to deposition on the interior of blood vessels. It is therefore believed that AGE-lipids may be involved to varying degrees in atherosclerosis, stroke and other vascular disease.

For instance, oxidation of the lipid component of low-density lipoprotein (LDL) results in the loss of the recognition of the apo B component by cellular LDL receptors, and in the preferential uptake of oxidized-LDL(ox-LDL) by macrophage "scavenger" receptors. The enhanced endocytosis of ox-LDL by vascular wall macrophages transforms them into lipid-laden foam cells that characterize early atherosclerotic lesions.

The "family" of AGEs includes species which can be isolated and characterized by chemical structure; some being quite stable, while others are unstable or reactive. AGE-lipids may also be stable, unstable or reactive.

When used with reference to endogenous lipids, AGE-lipid compounds are typically formed non-enzymatically in vivo. However, AGE-lipid compounds can also be produced in vitro by, e.g., incubating a mixture of a reducing sugar and a suitable lipid, e.g., a lipid bearing an amino group, or by other methods in vitro, such as chemical coupling of AGEs and AGE models to biological macromolecules.

The reaction between reducing sugars and the reactive groups of lipids may initiate the advanced glycosylation process. This process typically begins with a reversible reaction between the reducing sugar and the reactive group to form a Schiff base, which proceeds to form a covalently-bonded Amadori rearrangement product. Once formed, the Amadori product undergoes further rearrangement to produce the AGE-modified compound.

Although these reactions occur slowly, lipids may accumulate a measurable amount of AGEs in vivo. The resulting AGE-lipids may reduce the structural and/or functional integrity of organs and organ parts, modify the metabolism, or otherwise reduce or impair host function.

As stated in patent application Ser. No. 07/887,279 (filed May 21, 1992) (now abandoned), the formation of AGE-lipids is believed to presage atherogenesis and to induce fatty acid oxidation. Correspondingly, it was disclosed that aminoguanidine, an established inhibitor of protein advanced glycosylation also inhibits AGE-lipid formation.

The parent application also disclosed that aminoguanidine reacts directly with malonyl dialdehyde (MDA)-like fatty acid oxidation products, to inhibit the role that they play in continued atherogenesis. This finding was further confirmed in Picard et al. (1992) *Proc. Natl. Acad. Sci. USA*, 89:6876–6880, published in August, 1992, and after the filing date of the said parent application. Picard et al. focused their study on the reaction between MDA and apolipoprotein B (apo B), a protein component of LDL, and performed experiments to determine the ability of aminoguanidine to bind preferentially to MDA to prevent its conjugation to apo B. To establish the environment for these experiments, the authors induced lipid peroxidation by incubation with endothelial cells or with $Cu^{2+}$. The Picard et al. experiments were cumulative with experiments presented earlier by applicants with respect to this specific mechanism of aminoguanidine action, but are limited by the specific in vitro environment chosen, as the physiological oxidation of lipids to form the reactive aldehydes to which aminoguanidine is confirmed to bind in the context of the present invention, will not occur by the means utilized in the article.

More particularly, in vitro studies suggest that the oxidative modification of lipids proceeds via free radical-mediated oxidation of unsaturated bonds that are present within fatty acid residues (12, 13). Polyunsaturated fatty acids are particularly sensitive to oxidation because methylene hydrogens located between paired double bonds are easily abstracted by radical-catalyzed reactions. Diene conjugation occurs and hydroperoxides form. This is followed by fatty acid decomposition, the formation of reactive aldehydes, and in the case of LDL, the covalent modification of apoprotein residues (12, 14, 15).

The biochemical processes that initiate lipid oxidation in vivo remain poorly understood. Triplet oxygen is a poor oxidant under normal, physiological conditions and significant oxidation of LDL in vitro occurs only after the addition of micromolar concentrations of divalent metals such as copper. Lipid oxidation is prevented completely in these incubations by the inclusion of metal chelators such as EDTA (15). LDL oxidation also occurs in diverse cell culture systems and can be inhibited partially by pharmacological blockade of cellular lipoxygenases (16). The precise role of reactive oxygen species in the oxidative modification of lipids in vivo has not been determined, however. Low trace metal concentrations, the high availability of ligands that form tight coordination complexes with metals, and the abundant anti-oxidant capacity of plasma suggest that metal-catalyzed autoxidation and reactive oxygen species play little, in any role in mediating lipid oxidation in vivo (17–19). Further studies confirming the significance of these findings was presented in application Ser. No. 08/029,417 (filed Mar. 11, 1993).

The work discussed above and reviewed later on herein has prompted a further focussed consideration of the etiology of stroke, inasmuch as this condition is frequently the result of atherogenesis. Stroke caused by the abrupt development of cerebral ischemia is the third leading cause of death in the United States. The American Heart Association estimates that there are approximately three million stroke survivors in the United States, most of whom are disabled. Accordingly, the cost of this illness to society in both health care and lost productivity is enormous, by one estimate exceeding 14 billion dollars per annum. Moreover, patients with diabetes mellitus fare less well than non-diabetics with stroke, because they incur more extensive tissue death as compared to non-diabetics after occlusion of a cerebral artery. The extended complications of stroke represent a major problem for diabetics, and adversely influence both quality of life, and morbidity and mortality. The devastating complications of stroke in the diabetic population will assume even greater importance in the coming years, as larger numbers of diabetics survive into their later years when the frequency of stroke increases. Interest in improving the quality of life for these patients has fostered aggressive study aimed at improving treatment. But an incomplete understanding of the pathogenesis of cerebral infarction in diabetics hampers progress in this area, and lends a sense of urgency to identifying responsible factors.

Although a number of factors have been implicated in enhancing diabetic stroke-related neurotoxicity, a complete understanding of the biochemical basis for increased stroke size in diabetes remains elusive. Recent investigation into the pathogenesis of stroke indicates that a number of factors may directly influence the volume of brain infarction after occlusion of a cerebral artery. These studies suggest that such neurotoxic factors can transform ischemic but potentially viable brain tissue into an irretrievably infarcted lesion, resulting in larger strokes both in terms of parenchymal necrosis and corresponding functional impairment.

Accordingly, we began to evaluate the hypothesis that diabetes-induced biochemical changes may worsen stroke. It is well known that once a cerebral artery is occluded by a thrombus or embolus, the ultimate size of the resulting infarction is dependent upon a series of pathogenic events occurring in the "ischemic penumbra," the hypoperfused shell of brain that surrounds the densely infarcted zone. Progressive cell neuronal death occurs in the penumbra for hours subsequent to arterial occlusion. Ultimately therefore, factors that modulate neuronal cell death may either attenuate or amplify the size of the resultant stroke.

Early investigators presumed that disruption of a continuous supply of glucose and oxygen to neurons caused cell death by an "energy shortage." But studies by others have suggested that ischemic lesions caused by cerebral arterial occlusion are actually composed of a densely ischemic focus surrounded by a less densely ischemic "penumbral zone". Although the neurons in the dense core are destined to die within minutes, the cells in the penumbra are potentially viable for up to 8 hours. Neuronal death in the penumbra occurs not by rapid energy depletion, but rather by a complex cascade of metabolic and chemical events that mediate neuronal death. This cascade is initially triggered by diminished regional blood flow, but thereafter becomes essentially self-propagating.

A list of the metabolic and biochemical factors implicated in neuronal death in the penumbra includes (but is not limited to) calcium, excitatory neurotransmitters, platelet-activating factor, nitric oxide (EDRF), superoxide radicals, acidosis, transmembrane ion flux, anaerobic glycolysis and cerebral edema. It is now generally accepted that neuronal death in the penumbra is mediated by specific events and factors. This understanding has facilitated development of pharmaceuticals that prevent neuronal death in this critical period. For instance, pharmacological protection against cerebral infarction in the penumbra has been achieved by administering glutamate antagonists that competitively inhibit glutamate binding to the NMDA receptor. Neurons continue to die for an extended period in the penumbra, but targeted therapy administered up to 2 hr after cerebral artery occlusion may confer neuronal protection. Similar success has been achieved with other therapies targeted to events in the penumbra (e.g., calcium channel blockers, PAF antagonists, free radical scavengers, and inhibitors of nitric oxide).

Despite advances in the understanding of stroke pathogenesis, and the identification of the critical role played by cytotoxic events in the penumbra, the pathogenic mechanisms of enhanced cerebral infarction in diabetic patients are unknown. Among the factors that have been proposed (e.g., increased procoagulant activities, micro- and macro-angiopathy, hyperlipidemia, decreased red blood cell deformability, and impaired cerebrovascular autoregulation), perhaps the most widely studied in clinical and experimental investigation is hyperglycemia. Early experimental studies suggested that elevated blood glucose levels during focal cerebral ischemia increase the size of the resulting infarction. These investigators speculated that tissue injury was enhanced by lactate produced from anaerobic glycolysis in the hypoxic penumbra. These experimental observations were supported by clinical studies showing a correlation between glucose levels on admission to the hospital and poor outcome from stroke.

This theory has not received general acceptance however, because elevated glucose levels occur as part of the catabolic stress response to an underlying illness. Thus, higher glucose levels may reflect a more severe stress response to a larger cerebrovascular lesion. Measurements of HbA1c levels in diabetic patients with stroke revealed no correlation with infarct severity, leading other investigators to suggest that the post-stroke hyperglycemia is reactive, derived from the stress response, and does not contribute to increased stroke size. Further complicating the hypothesis, glucose has also been found to confer protection against neuronal death in animal models of focal cerebral ischemia. To date therefore, the role of acutely elevated high glucose levels in the complications of diabetic stroke remains unproven.

Advanced glycation endproducts (AGEs) have been implicated in the development of diabetic complications such as accelerated atherosclerosis, renal dysfunction, and neuropathy. AGE modifications accumulate by non-enzymatic reactions as permanent adducts and cross-linking structures on long-lived body proteins (for instance, collagen) as a function of age and glucose concentration, so that chronically or episodically elevated blood glucose levels in diabetic patients result in an accelerated linear accretion of AGE modifications to tissue proteins over time. AGE-modified proteins in tissues may subsequently undergo receptor-mediated and/or proteolytic cleavage into smaller, reactive AGE-peptides which are released into the circulation where they may ultimately either re-attach covalently to tissue proteins, or undergo elimination from the circulation by the kidneys. Previous observations suggest that high levels of AGE-proteins and AGE-peptides may enhance tissue damage directly by chemical crosslinking and adduct formation and indirectly by binding to AGE-specific receptors present on macrophages, endothelium, and other cell types.

AGE receptor-mediated responses mediate capillary leakage, cytokine production, enhanced procoagulant activity on the endothelial surface, and increased generation of reactive oxygen intermediates. AGE-mediated tissue damage may also occur when circulating AGE-proteins or AGE-peptides react directly to covalently cross-link with basement membrane proteins in the subendothelial space. The pathological effects of AGE deposition within the vasculature include increased vascular permeability and defective vasodilatory responses.

To this end, the present inventors have turned to the consideration of the role played by aminoguanidine, a known inhibitor of advanced glycosylation, in determining eventual infarct size after brain ischemia. The results presented herein suggest that this agent exerts effects additional to its known role as an inhibitor of advanced glycosylation, and that elucidation of the mechanism by which it exerts these effects can lead to the identification of additional agents having therapeutic effect in attenuating the size and severity of infarct size.

Accordingly, it is toward the presentation of these findings that the present disclosure is directed.

SUMMARY OF THE INVENTION

In one aspect of the invention that is the subject of the present application, a method and corresponding compositions are disclosed for the treatment of stroke, which method comprises administering a neuroprotective amount of an agent capable of averting the occurrence, or beneficially limiting or reducing the size and severity of an ischemic infarct, especially that resultant from polyamine damage, in both diabetic and non-diabetic individuals. Additionally, the present invention includes a method of identifying additional agents useful in such treatment by virtue of their ability to inhibit the oxidation of polyamines. More particularly, the method of the invention comprises administering to a patient in need thereof, a therapeutically effective amount of an agent selected from the group consisting of aminoguanidine, α-hydrazinohistidine, analogs of aminoguanidine, and pharmaceutical compositions containing any of the foregoing, all as recited in detail herein. Corresponding pharmaceutical compositions are likewise contemplated, including without limitation, the agents set forth herein as well as additional agents that may then be used in like fashion and for like purpose. This aspect of the invention also contemplates diagnostic procedures and materials including kits, that are useful and effective in the same pathological context.

It is therefore an object of the present invention to provide a method and related compositions for the diagnosis and treatment of stroke and similar maladies, that are based, in part, on the activity of certain agents that have been identified as AGE inhibitors.

It is a further object of the present invention to provide a method and related compositions for the treatment of stroke, and especially the reduction of infarct size resultant from AGE and polyamine damage.

It is a still further object of the present invention to provide a method of screening for agents capable of providing a neuroprotective effect and thus reducing the size and severity of infarct in stroke which comprises measuring the activity of a test agent as an inhibitor of the oxidation of polyamines, thus identifying an agent useful in reducing the size and severity of infarct during the treatment of stroke.

Other objects and advantages will be apparent from a consideration of the ensuing detailed description which proceeds with reference to the following illustrative drawings.

DETAILED DESCRIPTION OF THE INVENTION

Figure 1:
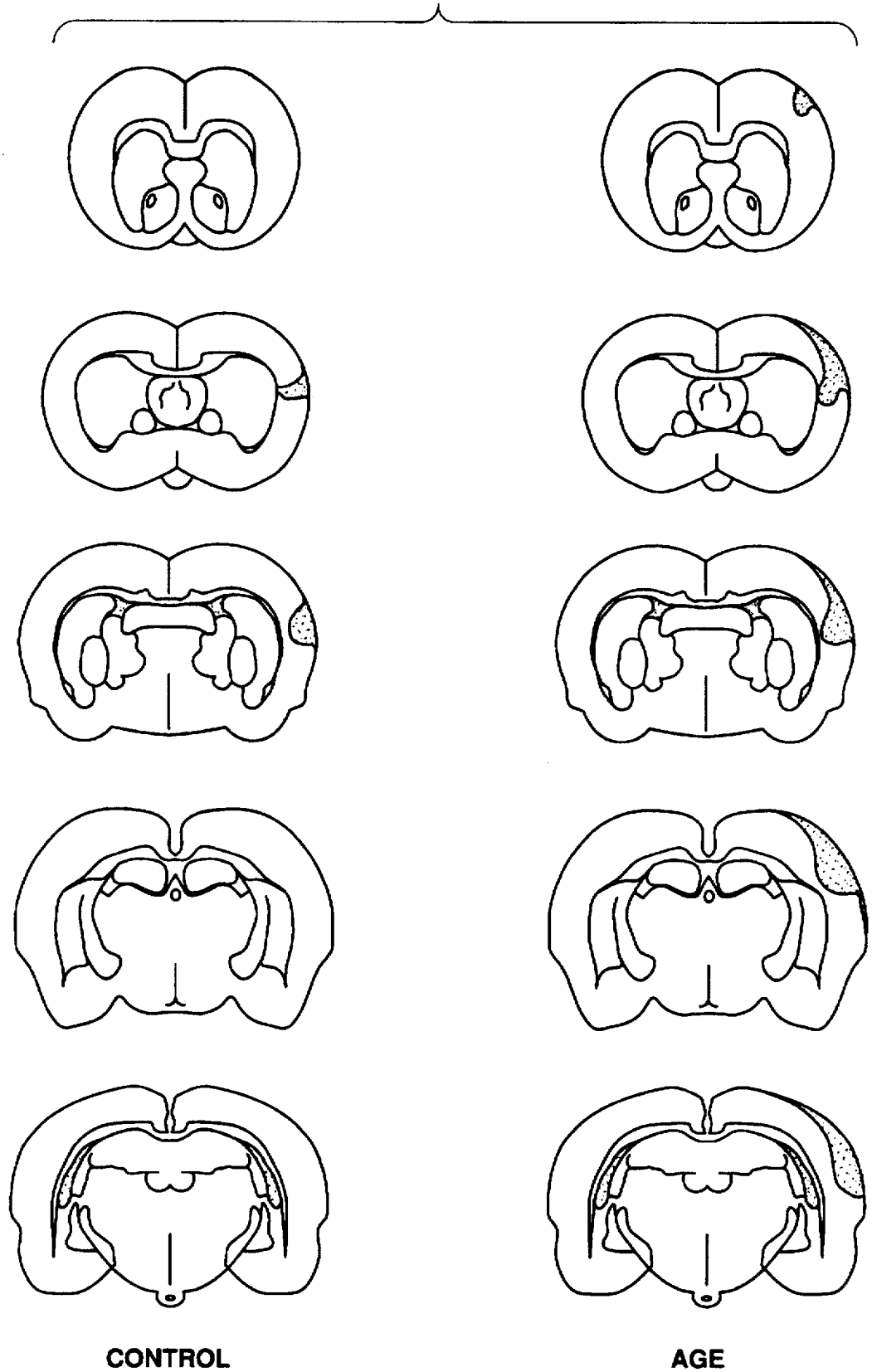
FIG. 1 presents the pattern of cerebral infarction observed at five stereotactic levels. Note that the infarcted region (stipple shaded area) on each section is limited to the cortex. Animals received either BSA or AGE-BSA thirty minutes prior to the onset of ischemia as described in the text.

Numerous abbreviations are used herein to simplify the terminology used, and to facilitate a better understanding of the invention. The following abbreviations are representative.

As used herein, the term "AGE-" refers to the compound which it modifies as the reaction product of either an advanced glycosylation endproduct or a compound which forms AGEs and the compound so modified, such as the lipid moiety. AGE-lipids can be formed in vitro by reacting a lipid as defined herein with an AGE, such as AGE-peptide, or either in vitro or in vivo with a compound such as a reducing sugar, e.g., glucose, until the lipid is modified to form the AGE-lipid.

The term "lipid" is used in the conventional sense to refer to materials that are soluble to a greater or lesser degree in organic solvents, like alcohols, and relatively insoluble in aqueous media. Thus, "lipid" includes compounds of varying chain length, from as short as about 2 carbon atoms to as long as about 28 carbon atoms. Additionally, the compounds may be saturated or unsaturated, and in the form of straight- or branched-chains or in the form of unfused or fused ring structures. Further, these lipid compounds can be optionally linked to other moieties, so long as at least one primary amino group, or other crosslinkable or otherwise reactive group, is present in the molecule.

The term "lipid-related materials" is used herein to encompass not only lipids as conventionally understood and as defined above, but those particles, aggregates and components thereof that are found in connection with lipid moieties. Examples of lipid-related materials included herein include fatty acids, sterol-type molecules, triglycerides, phospholipids, and lipoproteins including apolipoproteins. Preferred lipid-related materials include as the AGE-reactive groups one or more primary amino groups. It is particularly preferred to include at least one primary amino group reactive with AGEs and compounds which form AGEs.

The present invention extends to the discovery that certain compounds that have previously been identified as inhibitors of the advanced glycosylation of proteins, also inhibit the formation of lipid advanced glycosylation endproducts and, further, react directly with malonyl-dialdehyde-like fatty acid oxidation products. These inhibitors of advanced glycosylation endproduct formation in proteins are broadly set forth in U.S. Pat. No. 4,758,583, the disclosure of which is incorporated herein by reference. These compounds include compounds that react with a carbonyl moiety of an early glycosylation product. Representative of such advanced glycosylation inhibitors are aminoguanidine, lysine and α-hydrazinohistidine.

In addition to these specific compounds, other agents capable of inhibiting the advanced glycosylation or proteins have likewise been identified and are also utilizable to similarly inhibit the advanced glycosylation of lipids. These agents are set forth in U.S. Pat. Nos. 4,908,446; 4,983,604; 5,140,048; 5,175,192; 5,114,943; 5,137,916; 5,130,337; 5,100,919; and 5,106,877, the disclosures of which are likewise incorporated herein by reference.

Accordingly, where identified herein, the term "inhibitors of advanced glycosylation" is intended to encompass both the compounds such as aminoguanidine, lysine and α-hydrazinohistidine, and other agents as generically expressed hereinabove and as may be contained in other related patent applications and patents issued subsequently to U.S. Pat. No. 4,983,604 and having reference thereto.

A further aspect of the present invention relates to the role of the above compounds and their analogs in the treatment of stroke and related maladies, such as those involving reperfusion injury or ischemia. As stated earlier and as demonstrated by data presented hereinafter, it has been found that AGE-modified proteins or peptides are neurotoxic factors that amplify the volume of permanent damage and necrosis following focal cerebral ischemia. The results of experiments shown in the Examples below indicate that administration of AGEs in clinically relevant amounts converted a typically small cerebral infarction following experimental occlusion of a middle cerebral artery into a significantly larger stroke. The magnitude of AGE neurotoxicity depended on the dose of AGEs administered, and the timing of administration. Aminoguanidine, an inhibitor of AGE cross-linking, prevented this apparent neurotoxicity of exogenous AGEs. Thus, the neurotoxicity-potentiating effects of AGEs contribute importantly to the pathogenesis of diabetic stroke, and that aminoguanidine effectively antagonizes AGE-mediated increases in infarct volume. The results presented herein demonstrate that aminoguanidine exerts a therapeutic effect and beneficially limits or reduces eventual infarct size and severity, unexpectedly even in instances where AGE levels are not abnormally elevated.

In accordance with these findings, the present invention extends to the treatment of stroke by the administration of a stroke-ameliorating or stroke-inhibiting amount of an agent capable of at least partially preventing brain damage, or averting the occurrence or reducing the size and severity of an ischemic infarct due, for example, to stroke, aneurism, cerebrovascular accident, apoplexy or other trauma. While not wishing to be bound to a specific theory of action, it is submitted that the activity of aminoguanidine in this instance may proceed in a manner that may or may not relate to the concentration of AGEs in the host or patient. In this context, it is possible and consequently within the scope of the invention that the stroke reducing or inhibiting activity of the present agents may proceed in an AGE-dependent or AGE-independent manner.

The present invention therefore extends to methods for the treatment of stroke and to corresponding pharmaceutical compositions, comprising and including without limitation as active ingredients the inhibitors of advanced glycosylation enumerated herein, such as aminoguanidine, lysine, α-hydrazinohistidine, and the analogs thereof.

Within minutes after cessation of local cerebral blood flow, a region of densely ischemic brain tissue becomes infarcted and dies. This infarcted core is surrounded however, by a zone of ischemic but potentially viable tissue termed the "ischemic penumbra," which receives suboptimal perfusion via collateral blood vessels. The volume of the penumbra that ultimately becomes infarcted after an acute arterial occlusion is determined by a variety of factors that mediate neurotoxicity within this zone during the hours following interrupted blood flow. The nature of these factors (including glutamate, superoxide radicals, and nitric oxide) is only partially understood, as are the complex interactions that will determine whether ischemic tissue will die or recover. Some of these factors are intrinsic to the locus of ischemia, and others are delivered to the penumbra via the circulation. The net result of signalling interactions between these factors can greatly enhance neuronal cytotoxicity in the ischemic penumbra, causing a significantly larger volume of brain damage and necrosis, with corresponding increases in functional damage. The present results indicate that AGE-proteins, which are intrinsic to normal tissues and serum and significantly increased in senescence and diabetes, are neurotoxic in the ischemic penumbra, and may participate in mediating increased volumes of cerebral infarction during focal cerebral ischemia.

The molecular basis of AGE-mediated neurotoxicity is unknown, but one possible mechanism is through AGE-mediated induction of secondary signalling pathways. It has previously been shown that cellular recognition and uptake of AGE-modified molecules induces the expression of MRNA for TNFα, IL-1, IL-6, and other growth factors, and the production of reactive oxygen intermediates. These cytokine and reactive oxygen intermediates have been implicated in increasing tissue injury during ischemia. The AGE-mediated induction of these mediators is down-regulated within hours, which may account for a window of maximal neurotoxicity within hours after exposure to AGEs. Although serum TNFα levels were not elevated in the present study, it is plausible that the neurotoxicity of AGEs is mediated through TNFα or another secondary signal produced locally in tissues. This proposed mechanism is also consistent with the findings that AGEs administered 24 hours before interruption of cerebral blood flow do not enhance stroke volume, presumably because the short-lived AGE-induced signals are already downregulated before the tissue is made ischemic. When administered 30 minutes after the artery has already been occluded, the AGE-proteins would presumably have only restricted vascular access to the ischemic region, and may not have triggered the production of sufficient neurotoxic secondary signals so as to significantly affect infarct size. The molecular identity of putative secondary neurotoxic mediator(s) induced by AGE-proteins is presently under investigation.

Previous studies addressing the pathogenesis of increased stroke size in diabetic patients have implicated a number of factors including increased procoagulant activities, micro- and macro-angiopathy, hyperlipidemia, decreased red blood cell deformability, impairment of cerebrovascular autoregulation, and hyperglycemia. These studies indicate that AGEs may also participate in the development of increased cerebral infarct damage in diabetics. AGE levels are known to be increased in serum proteins and lipoproteins (LDL) of diabetic patients with or without renal dysfunction. From the present data it can now be predicted that the onset of cerebral ischemia in a patient with elevated serum AGE levels would be associated with the development of a larger cerebral infarction than would otherwise occur. Further, serum AGE-protein or AGE-ApoB/LDL levels can be used clinically to identify a subpopulation of diabetic patients at increased risk for catastrophic stroke.

Aminoguanidine has previously been shown to reduce the accumulation of exogenously administered AGE-peptides in the extravascular space (52–54). The present results now suggest that aminoguanidine also confers protection against the neurotoxic effects of AGEs in focal cerebral ischemia. Although the molecular mechanism of neuroprotection has not been precisely determined in this study, it is plausible that by reducing AGE-protein cross-linking with basement membrane proteins, aminoguanidine reduced the production of secondary neurotoxic signals. Another possible neuroprotective mechanism of aminoguanidine is by inhibiting the inducible form of nitric oxide synthase (iNOS), since nitric oxide has been implicated in mediating neuronal cell death during cerebral infarction. Recent investigations by Iadecola et al., Soc. Neurosci. Abst., 20, 1479 (1994) of the role of NO in focal stroke however, indicate that the expression of iNOS does not begin to increase until nearly 24 hours after the onset of cerebral ischemia. To the contrary, the present study shows an acute neuroprotective effect of aminoguanidine administered during the early periods of ischemia (and well before the reported period for increases in iNOS), so that it is unlikely that the protective effects of aminoguanidine were due to inhibiting iNOS. Further evidence suggesting that the effects of aminoguanidine were independent of NOS inhibition can be determined from our observations that aminoguanidine did not prevent the AGE-mediated increases in regional cerebral blood flow. To the extent that this redistribution of blood flow is mediated by nitric oxide, aminoguanidine did not attenuate the NOS activity present in cerebral blood vessels.

A further mechanism for the neuroprotective effects of aminoguanidine is through its activity in abolishing the toxicity of polyamine metabolism by inhibiting the formation of toxic aldehydes. Since the oxidation of polyamines is enhanced in cerebral ischemia, and the production of these toxic metabolites further enhances neuronal killing, it has been determined that the neuroprotective effects of aminoguanidine are also the result of inhibition of polyamine metabolism in focal cerebral ischemia. This potential mechanism of aminoguanidine-mediated neuroprotection may be effective even in the absence of exogenously added or abnormally elevated AGE levels. AGE-modified proteins and peptides are detectable in the circulation of normal (non-diabetic, non-senescent) animals including humans, and we have recently found that aminoguanidine attenuates focal cerebral infarction in normal animals during more prolonged ischemia (68). Thus, there may be more than one independent protective mechanism for aminoguanidine in stroke, since during the later stages of infarction, up to 48 hours after arterial interruption, the neuroprotective effects of aminoguanidine may be mediated by inhibition of iNOS.

The ability of an agent to inhibit polyamine oxidation provides an additional therapeutic mechanism in the treatment of stroke since it results in a reduction in the size and severity of the infarction. Obviously, agents possessing activity both as AGE-inhibitors and as inhibitors of such polyamine oxidation are especially desirable therapeutic agents.

The present invention thus includes a method a screening for an agent capable of providing a neuroprotective effect and thus reducing the size and severity of infarct size in stroke which comprises administering a test agent concurrent with, or subsequent to, an infarct-producing amount of a polyamine and measuring the resultant decrease in infarct size vis-a-vis a control dose of the infarct-producing amount of the polyamine. Such testing can reveal agents which are useful in the treatment of this aspect of stroke.

In Examples 1–3, the activity of aminoguanidine in the lessening of the effects of stroke is presented and demonstrated. Example 4 demonstrates the infarct volume reduction during stroke by an inhibitor of diamine oxidase, chloroquine. Example 5 demonstrates that the neuronal cytotoxicity of spermine is serum-dependent and that aminoguanidine, as well as other agents which inhibit the enzymes responsible for polyamine oxidation, inhibit this spermine-mediated neuronal cytotoxicity.

Further details of the above and additional studies are presented below.

EXAMPLE 1

When a cerebral vessel is occluded by embolism or thrombus, the extent of the resultant infarction is in part dependent upon the severity of events occurring within the ischemic penumbra, the shell of viable but hypoperfused tissue with potential to survive that surrounds the anoxic and densely infarcted core. Advances in stroke therapy have focused on understanding the pathobiology of cytotoxic factors in the penumbra in order to enhance neuronal survival. Diabetic patients are known to incur more severe strokes than nondiabetics, but the mechanisms of increased neuronal cytotoxicity in diabetic stroke are unknown.

Advanced glycosylation endproducts (AGEs) are reactive, crosslinking, covalent adducts formed by the nonenzymatic reactions of free glucose with protein amino groups in tissues including brain and cerebral vessels. Diabetics have elevated circulating and tissue levels of AGEs which have been implicated in the genesis of diabetic complications. For instance, AGEs have been shown to induce capillary leakage, to increase cytokine production, and to promote procoagulant activity on the endothelial surface. Our experiments show that exogenously supplied AGEs cause a 9-fold increase in infarct size in a model of focal cerebral ischemia. These data suggest that naturally formed AGEs may play a role in the pathophysiology of increased stroke in diabetics.

In an effort to inhibit the effects of AGEs on brain damage in cerebral ischemia, aminoguanidine, a compound that reacts with glycation adducts to prevent chemical crosslinking, was employed. The results that follow suggest that aminoguanidine significantly mitigates the stroke-enhancing properties of exogenously supplied glycosylation adducts. In addition, aminoguanidine decreases experimentally-induced ischemic infarct volume in the absence of exogenous AGEs, suggesting a potential therapy for stroke and related maladies involving of including ischemia or roperfusion injury, that damage brain, heart, bowel or other organs or tissues, including as examples, peripheral vascular occlusion injury, diabetic retinopathy and damage attendant to angioplasty.

MATERIALS AND METHODS

AGE-albumin was prepared by incubating glucose with bovine serum albumin (Sigma, St. Louis, Mo.) and purifying it by previously established methods. Aminoguanidine was supplied by Regis Chemical Company, Morton Grove, Ill.

Male Lewis rats, 270–320 g, were anesthetized with ketamine (120 mg/kg). Through a midline ventral cervical incision, both common carotid arteries were exposed and the right was ligated. In some experiments (where indicated) the tail artery was cannulated to monitor mean arterial pressure and heart rate and provide serial measurements of arterial pH, oxygen, carbon dioxide, and glucose. The right middle cerebral artery was exposed through a 1 mm burr hole drilled approximately 2 mm rostral to the fusion of the zygome with the temporal bone, and elevated 1 mm from the rhinal fissure where it was severed with a cautery. Within 5 minutes of severing the artery, the left common carotid artery was temporarily occluded for 30 minutes or 1 hour (see Table 5, below). Twenty-four hours after experimentally-induced ischemia, brains were removed and coronally sectioned at 1 mm intervals with a brain slicer. Slices were immersed in 2,3,5-triphenyltetrazolium (TTC) (2% in NaCl, 154 mM) for 30 minutes at 37° C. to stain viable tissue. Infarct volume was determined by planimetry on projected images of photographed brain slices, and data expressed as a percentage of total right hemisphere volume infarcted. Statistical analysis on data was performed using a paired T-test.

RESULTS AND DISCUSSION

To examine whether aminoguanidine mitigates against the stroke-enhancing effect of AGEs, we studied the effect of co-administration of AGE-modified albumin (AGE-alb) and aminoguanidine on infarct size, and the effect of aminoguanidine on stroke in the absence of exogenous AGE (see Table 1).

In the first experiment, AGE-alb (235 mg/kg, iv) or albumin (235 mg/kg, iv) was administered 2 hours before severing the right middle cerebral artery. In some animals, aminoguanidine (450 mg/kg, iv) was given with the AGE-alb infusion. As shown in Table 1, aminoguanidine prevented the AGE-alb mediated increase in stroke size as compared to AGE-alb administered alone. These data suggested that aminoguanidine interferes with the cascade of cytotoxic effects elicited by AGEs in the ischemic penumbra.

The next experiment addressed whether aminoguanidine protects against neuronal death, even in the absence of exogenous AGEs. Accordingly, three groups of animals were studied: one received aminoguanidine (160 mg/kg, ip), 30 minutes prior to severing the right middle cerebral artery; another received aminoguanidine (160 mg/kg, ip) 15 minutes after artery severing; and the third group received saline (3 ml/kg, ip) 30 minutes before artery severing. As shown in the table, animals treated with aminoguanidine had significantly decreased infarct size (1.3±0.6%) compared to saline-treated controls (6.0±0.7%, p<0.05). The protective effect of aminoguanidine was significant even when aminoguanidine was given after severing the artery (1.2±0.4%).

Because a number of physiological responses have been implicated in mediating stroke size after cerebral artery occlusion, we next explored whether aminoguanidine altered blood pressure, heart rate, blood glucose, pH, or oxygen and carbon dioxide tensions at 30 minute intervals before and after stroke. Statistical analysis revealed no significant differences between groups suggesting that aminoguanidine does not exert its effects by altering these physiological parameters. When considered together, these data suggest that the presence of aminoguanidine in the ischemic penumbra may reduce the size of focal cerebral infarction. Likewise, aminoguanidine and its analogs may be used to limit reperfusion injury and other ischemic injury to heart, bowel or other organ or tissue.

TABLE 1

AMINOGUANIDINE ATTENUATES FOCAL STROKE

| EXPERIMENT | GROUP | n | STROKE SIZE (1% HEMISPHERE INFARCTED) | p < .05 vs. CONTROLS |
|---|---|---|---|---|
| I (30 min. left carotid occlusion) | Control (Albumin) | 6 | .6 ± .2% | — |
| | AGE-Albumin | 6 | 5.4 ± 2.0% | Yes |
| | AGE-Albumin + Aminoguanidine | 6 | 1.2 ± .5% | No |
| II (60 min. left carotid occlusion) | Control (Saline) Aminoguanidine | 6 | 6.0 ± .7% | — |
| | Aminoguanidine (30' pre-sever) | 6 | 1.3 ± .6% | Yes |
| | Aminoguanidine (15' post-server) | 6 | 1.2 ± .4% | Yes |

EXAMPLE 2

By this experiment, it was determined that AGE-modified proteins or peptides are neurotoxic factors that amplify the volume of permanent damage and necrosis following focal cerebral ischemia. The results presented here show that administration of AGEs in clinically relevant amounts converted a typically small cerebral infarction following experimental occlusion of a middle cerebral artery into a significantly larger stroke. The magnitude of AGE neurotoxicity depended on the dose of AGEs administered, and the timing of administration.

MATERIALS AND METHODS

Bovine serum albumin (BSA) (Fraction V, low endotoxin), glucose, and 2,3,5-triphenyltetrazolium were purchased from Sigma (St. Louis, Mo.). Aminoguanidine was provided by Alteon Inc. (Ramsey, N.J.). All animal protocols were reviewed and approved by the Institutional Animal Care and Use Committee as conforms with the recommendations of the National institutes of Health. AGE-modified bovine serum albumin (AGE-BSA) was prepared by a modification of previously described methods (52–54); endotoxin content was measured by Limulus amoebocyte assay (E-toxate, Sigma) and found to be <0.2 mg/ml. AGE content in samples and in serum was assessed by ELISA (35,36). The AGE-BSA (65 AGE U/ml) employed in these studies was prepared at a final concentration of 30 mg/ml in PBS.

Animal model of focal middle cerebral artery infarction

Focal cerebral ischemia was induced by modification of previously described methods (55–58). Briefly, male Lewis rats, 270–300 g, were given food and water ad libitum before and after surgery. Animals were anesthetized with ketamine (120 mg/kg i.m.), allowed to breathe spontaneously, and body temperature maintained at 35.5°–36.5° C. with a heating blanket. The ventral neck and the area between the right eye and ear were shaved, and the left common carotid artery exposed through a midline ventral cervical incision. The vagus nerve was preserved, and a loop of 4-0 silk placed around the artery for future manipulation. Next, the right common carotid artery was exposed and permanently occluded by double ligation with 4-0 silk. In some experiments (where indicated) the right common carotid artery was cannulated with polyethylene tubing connected via a pressure transducer to an oscilloscope for recording mean arterial pressure and heart rate. Arterial blood was also obtained for serial measurements of arterial pH, oxygen and carbon dioxide tensions, hematocrit, and glucose.

A microsurgical craniotomy was performed via a 1 cm right scalp incision made orthogonal to the line joining the external auditory canal and the lateral canthus of the right eye. The temporalis muscle was excised to expose the temporal bone and the zygoma. With the aid of the dissecting microscope, the right middle cerebral artery was exposed through a 2 mm burr hole drilled approximately 2 cm rostral to the fusion of the zygoma with the temporal bone. Drilling, performed under a continuous drip of normal saline to avoid transmission of heat to the underlying cortex, continued until a thin shell of bone remained. This bone was carefully removed with a micro-hook and micro-forceps to avoid injury to the underlying structures. The right middle cerebral artery (MCA) was exposed by cutting the dura with a 30 gauge needle in a location approximately 1 mm from the rhinal fissure. The right middle cerebral artery was elevated from the cortical surface using a micromanipulator and a 20 micron tungsten wire hook, and an electrocautery tip was gently applied to the hook. The application of heat quick IV cauterized and severed the artery which fell back to the cortex with no underlying cortical injury. Surgical gelfoam was placed over the craniotomy defect and the skin was closed with a running vicryl suture. Within 5 minutes of severing the right middle cerebral artery, the left common carotid artery was temporarily occluded for 30 minutes; the neck incision was then closed with a running vicryl suture and the animals returned to their cages for 24 hours with free access to food and water. After surgery, animals were somewhat clumsy but were able to walk, eat and drink.

Measurement of infarct volume

Infarct volume was measured using tetrazolium dye as previously described (55–58). Briefly, 24 hours after MCA severing, animals were anaesthetized and decapitated. Brains were quickly removed without perfusion and sectioned in the coronal plane at 1 mm intervals with a brain slicer. Slices were immersed and incubated in 2,3,5-triphenyltetrazolium (TTC) (2% in NaCl, 154 mM) for 30 minutes at 37° C. in the dark to stain for mitochondrial dehydrogenase activity. Brain infarctions were visualized as areas of unstained (white) tissue which were easily contrasted with adjacent viable tissue which stained red. Stained brain sections were then placed in buffered 10% formalin, photographed, and infarct area in each slice determined by planimetry on projected images of the brain slices. Infarct volume expressed as a percentage of the right hemisphere volume was calculated by the equation: [sum of infarct areas from all sections of a given animal]×[sum of total right hemisphere area from the same sections]$^{-1}$×100. In separate experiments, the volume of infarct determined by TTC staining was verified by histological analysis of serial brain sections stained with hematoxylin and eosin. Data were analyzed by a factorial analysis of variance.

Measurement of regional cerebral blood flow

Cerebral blood flow was measured using microspheres (59,60). Briefly, rats were anesthetized with ketamine and the femoral artery cannulated with PE-50 polyethylene tubing (Clay Adams, Parsippany, N.J.). Animals received BSA or AGE-BSA by intravenous injection into the tail at the doses and times indicated. The right middle cerebral artery was exposed and severed as outlined above. Thirty minutes later $^{141}$Ce-labeled microspheres (15 μm) were administered into the left ventricle of the heart as a suspension (300,000–400,000/ml in dextran 10%; 0.3 ml per injection) via a 23 gauge needle connected to PE-50 polyethylene tubing. The microspheres were infused over 20 seconds, and simultaneously a reference arterial blood sample was withdrawn from the femoral artery catheter at a rate of 400 μl/minute for one minute. The anesthetized rats were then decapitated, the brains removed, cut into 1 mm thick slices in the brain slicer, and the hemispheres separated. The slices from right and left hemispheres were then placed into tared counting tubes, weighed, and the radioactivity counted in a gamma counter. Cerebral blood flow to the ischemic penumbra was calculated from the equation: cbf=[(reference blood withdraw rate, ml/min)(cpm in hemisphere)][(hemisphere weight) (cpm in reference blood)]$^{-1}$.

Results

Serum AGE clearance following administration of exogenous AGE-BSA. It has recently been reported that circulating AGE levels are elevated in diabetic patients (61,62, 36), but the influence of elevated serum AGEs on the pathogenesis of cerebral infarction is unknown. As an initial step in establishing an animal model where the neurotoxic effects of elevated circulating AGEs levels could be directly assessed, the serum clearance of AGEs in rats given exogenous AGE-BSA was examined. Lewis rats received AGE-BSA (235 mg/kg) as a bolus injection via a surgically implanted carotid artery catheter. Total serum AGE levels were determined by ELISA on serum samples obtained at 10, 30, 60, 120, 180 and 240 minutes after AGE-BSA administration. Peak AGE levels (120±11 U/ml; mean±s.e., n=4 animals per group) were detected 10 minutes after administration. Within 120 minutes, circulating AGE levels had fallen to baseline (20±3 U/ml); serum half-life was estimated to be 60 minutes.

Neurotoxic effects of AGEs during focal cerebral ischemia

Animal models of middle cerebral artery occlusion have been widely used for the study of stroke because they closely mimic the effects of focal stroke in man (55,63). In the present model, the middle cerebral artery was microsurgically interrupted just distal to the lenticulostriate vessels, thereby limiting the zone of infarction to the cortex. Initially, the neurotoxic effects of AGE-BSA administered intravenously 30 minutes prior to microsurgically interrupting the middle cerebral artery was studied. FIG. 1 displays graphically a typical infarction in a control and an AGE-treated animal. Systemically administered AGEs were markedly neurotoxic, as evidenced by significantly larger infarct volumes in AGE-treated animals (AGE-BSA=3.2±1.1%) as compared to BSA-treated controls (BSA=0.6±0.2%; p<0.05). The neurotoxic effects of AGEs in this model were readily apparent as increased areas of infarction present on comparable stereotactic brain sections (FIG. 1). Moreover, AGE administration caused the zone of infarction to extend over a larger number of stereotactic brain sections (FIG. 1).

Figure 2A:
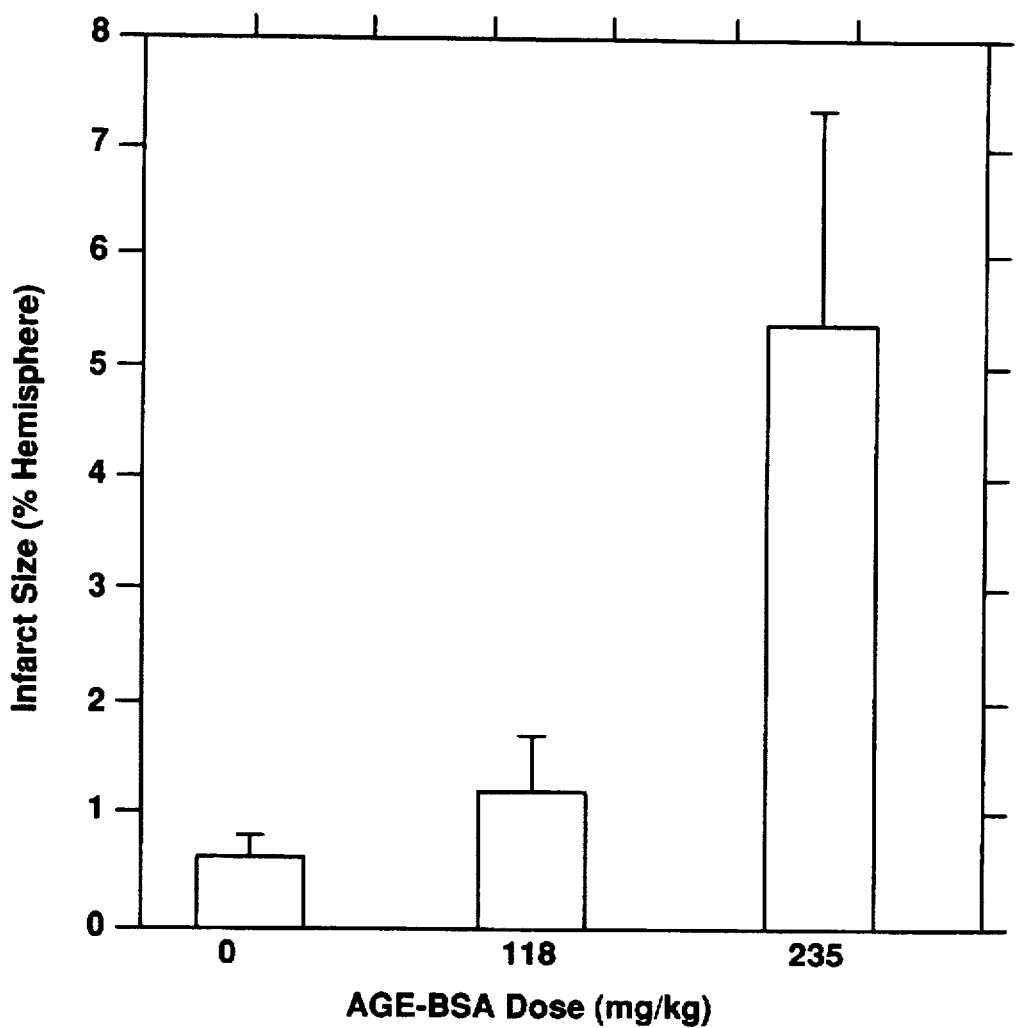
FIG. 2A is a bar graph showing the time-dependence of the stroke-enhancing effects of AGEs. AGE-BSA (235 mg/kg) was administered at the times shown relative to the onset of ischemia at time=0. Data shown are the volume of hemisphere infarcted expressed as a percentage of the entire hemispheric volume. (Mean±s.e., n=6–8 animals per group).

Experiments to bracket the time course of the neurotoxic effects of AGE-BSA in this model were performed. Administration of AGE-BSA two hours before cutting the artery caused a significant increase in infarct volume (5.4±2.0%; P<0.05 versus controls) (FIG. 2a). Stroke volume was also significantly increased by AGE-BSA administration 30 minutes prior to cutting the artery. The stroke-enhancing effects of AGEs were not observed however, when the AGE-BSA was administered either twenty-four hours prior to cutting the artery, or 30 minutes after the artery was cut (FIG. 2a). These results give evidence that the neurotoxicity of a single does of AGEs, systematically administered in conjunction with focal cerebral ischemia, is a temporally restricted event, occurring when circulating AGE levels are increased immediately prior to the interruption of cerebral blood flow.

Figure 2B:
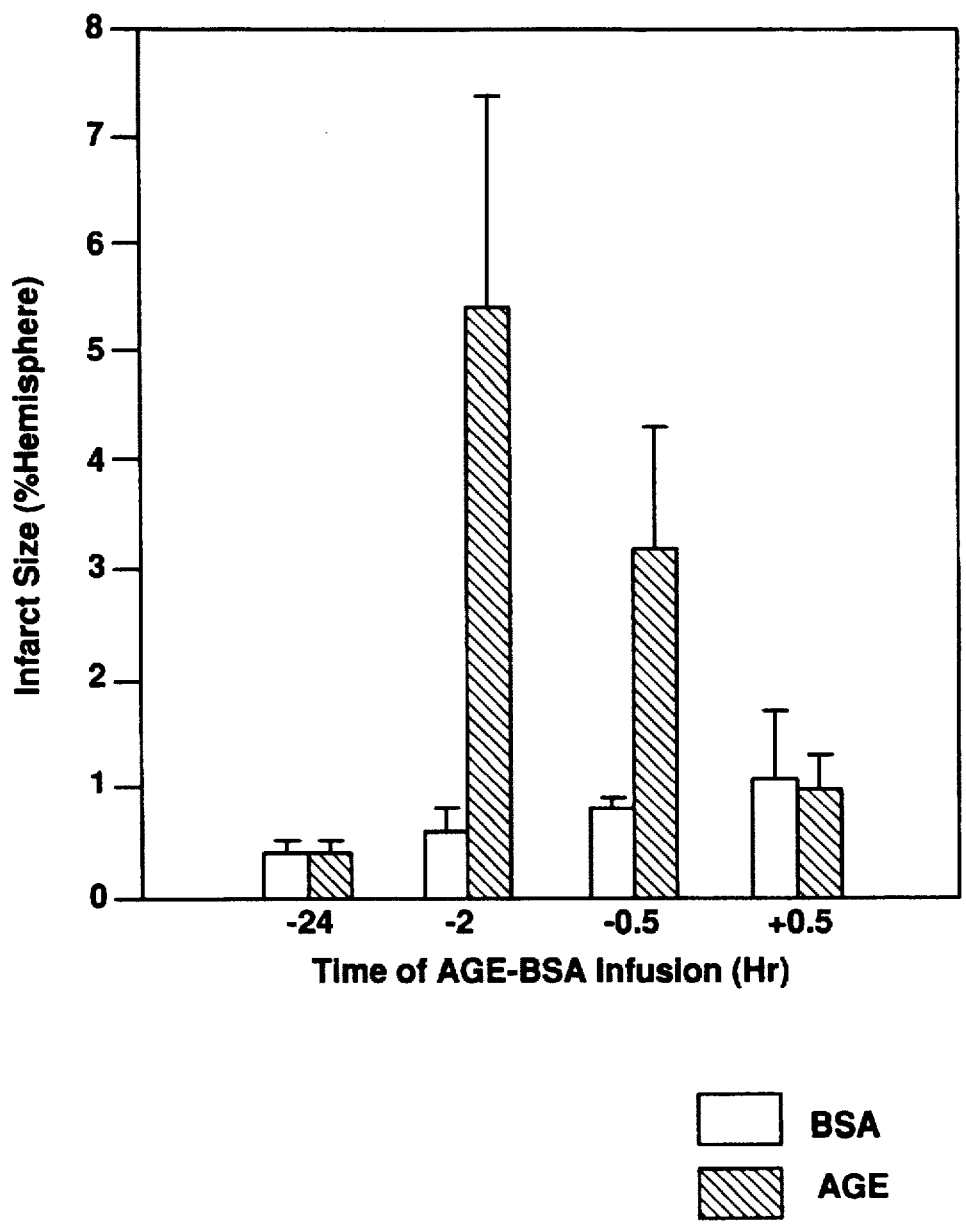
FIG. 2B is a bar graph showing the dose-dependence of the stroke-enhancing effects of AGEs. Two hours before the onset of ischemia, AGE-BSA was administered in the doses shown. Data shown are the volume of hemisphere infarcted expressed as a percentage of the entire hemispheric volume. (Mean±s.e., n=6–8 animals per group).

Separate experiments were performed to evaluate the relationship of AGE dose to the volume of resultant cerebral infarction. As a control for both total injectate volume and total quantity of albumin delivered, all animals received equal amounts of total albumin (235 mg/kg). Two hours before the middle cerebral artery was microsurgically divided, control animals received BSA only, but experimental animals received AGE-BSA mixed with BSA. As shown in FIG. 2b, the neurotoxic effects of AGE-BSA were dose-related, with larger doses of AGE-BSA causing larger cerebral infarctions. Considered together, these data indicate that exposure to elevated serum AGE levels just prior to cessation of cerebral blood flow results in larger strokes, the size of which is ultimately dependent upon the dose of AGEs administered, and the timing of AGE administration.

Effects of AGE administration on physiological parameters

A number of physiological parameters are known to correlate with an increased volume of cerebral infarction in this model of focal stroke. For instance, a fall in blood pressure predictably reduces cerebral perfusion in the collateral vessels perfusing the zone of ischemia and thereby increases infarct volume. Other parameters which increase stroke size in this model are: bradycardia, hyperthermia, hyperglycemia, hypoxia, acidosis, and hypercarbia. The effect of AGEs on these parameters was measured in a parallel group of animals in order to determine whether the neurotoxic effects of AGEs were attributable to AGE-mediated changes in these physiological parameters.

Animals received either AGE-BSA (experimental) or BSA alone (control) two hours before the middle cerebral artery was severed. Physiological parameters were measured at baseline (before the administration of BSA or AGE-BSA), again when the middle cerebral artery was cut (t=0), and at intervals thereafter as shown in Table 2 below. In agreement with previous experience with this model, animals in both the control and AGE groups developed a transient decrease in blood pressure and heart rate immediately after the middle cerebral artery was occluded; these temporary effects normalized within one hour. None of the physiological parameters were noticeably affected by administration of AGEs, and no statistically significant differences were observed between AGE-BSA and BSA alone (P>0.05, Table 2). These data suggest that the neurotoxicity of AGE-BSA is not mediated through changes in blood pressure or blood chemistry.

Effects of AGEs on regional cerebral blood flow

Blood flow to the ischemic cerebral cortex is derived from collateral blood vessels that are patent after blood flow through the occluded cerebral artery has ceased. Neuronal survival in the ischemic region is critically dependent upon the rate of regional cerebral blood flow from these collateral vessels, and any reduction of regional blood flow results in larger, more damaging infarctions (64,65). Cerebral blood flow is regulated in part by nitric oxide (NO), a potent vasodilator that is produced in the blood vessel wall, and it is implicated in the mediation of increased regional blood flow (66,67). Previously, it has been shown that chronic, repeated administration of AGE-BSA chemically inactivates the vasodilatory activity of NO in the systemic regulation of blood pressure, probably by local quenching (52, 24). Based on these observations, it is plausible in the present study that AGEs might diminish cerebral blood flow by inactivating NO in collateral cerebral vessels.

Experiments were performed to measure the effects of AGEs on regional cerebral blood flow in this model. As shown in Table 3, microsurgical interruption of the middle cerebral artery in BSA-treated controls reduced cerebral blood flow to a level that was 74% of the intact contralateral hemisphere. Surprisingly, rather than the predicted decrease, it was found that the administration of AGEs actually increased absolute cerebral blood flow in both the normal and infarcted hemispheres. Administration of AGE-BSA did not change the proportional reduction of cerebral blood flow between the intact and the infarcted hemisphere (Table 3). Since blood pressure was not altered (Table 2), these results suggest that administration of AGE-BSA mediated vasodilation of cerebral resistance vessels with a resultant increase in cerebral blood flow. Thus, the observed neurotoxic effects of AGE-BSA were not simply attributable to the inhibition of NO in cerebral vessels.

Neurotoxic effects of AGEs are inhibited by aminoguanidine

Figure 3:
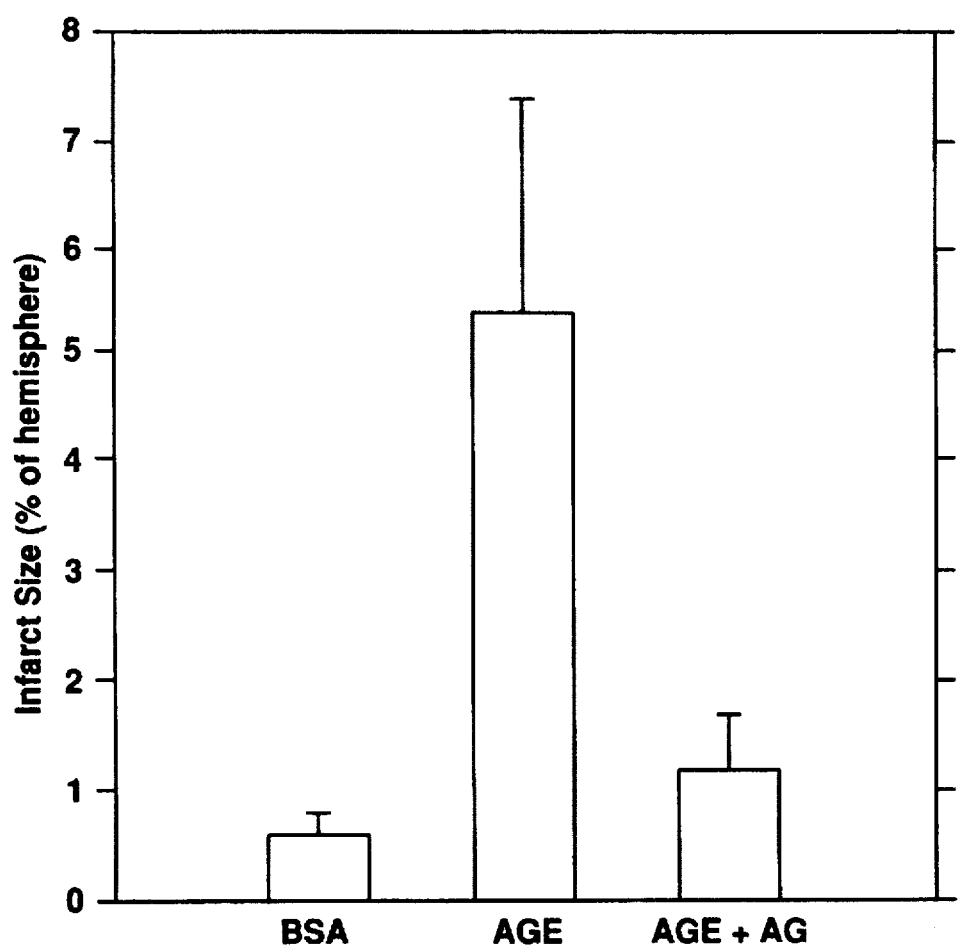
FIG. 3 is a bar graph showing that aminoguanidine attenuates the enhanced stroke volume associated with exogenous AGE administration. Two hours before the onset of ischemia, animals received either BSA (235 mg/kg), AGE-BSA (235 mg/kg) or AGE-BSA (235 mg/kg), and aminoguanidine (450 mg/kg). To control for total volume of injectates, all solutions were given in a final volume of 3.2 ml/kg. Data shown are the volume of hemisphere infarcted expressed as a percentage of the entire hemispheric volume. (Mean±s.e., n=6–8 animals per group).

AGE-peptides may be removed from the circulation via at least three pathways: i) interaction with cellular binding proteins or receptors; ii) clearance by the kidneys, and iii) by entering the extravascular space and chemically reacting with basement membrane proteins. Aminoguanidine inhibits the accumulation of exogenously administered AGEs in the subendothelium and attenuates the pathological effects of AGEs in tissues. An experiment was performed to assess whether aminoguanidine would also attenuate the neurotoxic effects of exogenously elevated serum AGEs in the present focal stroke model. Aminoguanidine treatment in conjunction with exogenous AGEs reduced total cerebral infarction volume by 78% as compared to AGE-treated controls that did not receive aminoguanidine (FIG. 3). The dose of aminoguanidine in this experiment did not significantly reduce the AGE-mediated increases of regional cerebral blood flow observed in either the infarcted hemisphere or the intact hemisphere (Table 3).

In summary, the present results give evidence that AGEs can be a neurotoxic factor that significantly determines infarct volume following focal cerebral ischemia. Aminoguanidine, an inhibitor of AGE-protein cross-linking, attenuated this AGE-mediated increase in stroke volume. These results indicate that therapeutics agents for diabetic stroke may be rationally based either on preventing AGE accumulation in serum and tissues during diabetes and aging, or on inhibiting AGE-mediated neurotoxic pathways.

TABLE 2

EFFECTS OF EXOGENOUS AGE-BSA ON PHYSIOLOGICAL PARAMETERS
* DATA ARE MEAN + S.E.; N = 4–6 PER GROUP
TIME AFTER MIDDLE CEREBRAL ARTERY OCCLUSION (MINUTES)

| GROUP | BASELINE | 0 | 30 | 60 | 120 |
|---|---|---|---|---|---|
| Control (235 mg/kg BSA) | | | | | |
| MABP (mm HG) | 110.5 ± 5.9 | 96.0 ± 2.2 | 85.3 ± 5.0 | 92.5 ± 5.6 | 96.0 ± 2.3 |
| pH | 7.33 ± 0.1 | 7.33 ± .01 | 7.35 ± .01 | 7.34 ± .02 | 7.34 ± 0.2 |
| $pCO_2$ (mm Hg) | 45.4 ± 1.0 | 45.1 ± 1.7 | 44.7 ± 2.0 | 38.9 ± 1.4 | 40.5 ± 1.8 |
| $pO_2$ (mm Hg) | 115.2 ± 13.9 | 90.4 ± 2.7 | 79.2 ± 9.3 | 100.3 ± 14.4 | 77.6 ± 11.0 |
| Hct (%) | 41 ± 1 | 42 ± 1 | 39 ± 1 | 39 ± 1 | 40 ± 1 |
| AGE (235 MG/KG AGE-BSA) | | | | | |
| MABP (mm Hg) | 102.5 ± 2.5 | 86.3 ± 2.8 | 84.0 ± 4.1 | 101.5 ± 1.0 | 106.0 ± 3.6 |
| pH | 7.32 ± .01 | 7.32 ± .01 | 7.32 ± .01 | 7.33 ± .01 | 7.36 ± .01 |
| $pCO_2$ (mm Hg) | 47.0 ± 1.8 | 42.8 ± 2.3 | 43.3 ± 1.9 | 38.1 ± 1.0 | 38.3 ± 1.9 |
| $pO_2$ (mm Hg) | 98.5 ± 9.0 | 92.6 ± 5.0 | 90.5 ± 5.0 | 91.3 ± 1 | 95.3 ± 8.3 |
| Hct (%) | 40 ± 1 | 39 ± 2 | 38 ± 1 | 36 ± 1 | 38 ± 1 |

* Differences between BSA and AGE-BSA were not significant (P > 0.05).

TABLE 3

EFFECTS OF AGES ON REGIONAL CEREBRAL BLOOD FLOW
ALL DATA ARE EXPRESSED IN ML/MIN PER 100 GRAMS TISSUE (MEAN + S.E.)

| Group (n = 4) | Left Hemisphere (Intact) | Right Hemisphere (Intact) | Ratio of Infarct/Intact (%) |
|---|---|---|---|
| BSA | 66 ± 5* | 48 ± 3* | 73 |
| AGE-BSA | 111 ± 6 | 86 ± 5 | 77 |
| AGE-BSA + Aminoguanidine | 91 ± 11 | 63 ± 6 | 69 |

*P < 0.05 versus AGE-BSA

EXAMPLE 3

To further ascertain the mechanism by which aminoguanidine functions as a neuroprotectant by modulation of the infarct size in stroke, the following experiment was conducted. In this study, Lewis rats (250–400 g) were anesthetized with ketamine and subjected to stereotactic injections of the biogenic polyamine spermine (SPM) in to the right parietal cortex and an equal volume (2 µl) of normal saline vehicle (NS) at a corresponding location in the left parietal cortex. Forty-eight hours later, the brain was sectioned into 1 mm coronal slices, stained with 2% tetrazolium red (30 minutes, 37° C.), and areas of necrosis determined by planimetry. The resulting area of necrosis produced by SPM 25 µg (5.00±1.67 mm$^3$, n=6) was significantly Larger than that produced by NS alone (0.10±0.08 mm$^3$, n=10) (P<0.05, ANOVA). To assess whether the coadministration of aminoguanidine (AG) might attenuate the neurotoxicity of SPM, rats received an injection containing a mixture of SPM 25 µg and AG 80 µg into the right hemisphere; the resulting volume of necrosis (0.70 0.44 mm$^3$, n=4) was significantly smaller than that produced by SPM 25 µg alone (P<0.05, ANOVA). These data indicate that SPM is neurotoxic when injected directly into the cerebral cortex and that AG protects against this neurotoxicity, thus resulting in modulation and inhibition of infarct size resultant from polyamine damage in stroke.

EXAMPLE 4

Using the rodent model of focal cerebral infarction described in Example 3 above, a microsurgical craniotomy was performed and the middle cerebral artery cut on one brain hemisphere. The ipsilateral carotid artery was permanently occluded, and the contralateral carotid artery was occluded for sixty minutes. Fifteen minutes after severing the artery, chloroquine was administered intraperitoneally as a single injection in a dose of 25 mg/kg. Twenty-four hours after severing the artery, the animal was euthanized, and the volume of infarction measured by planimetry as described hereinabove.

Figure 4:
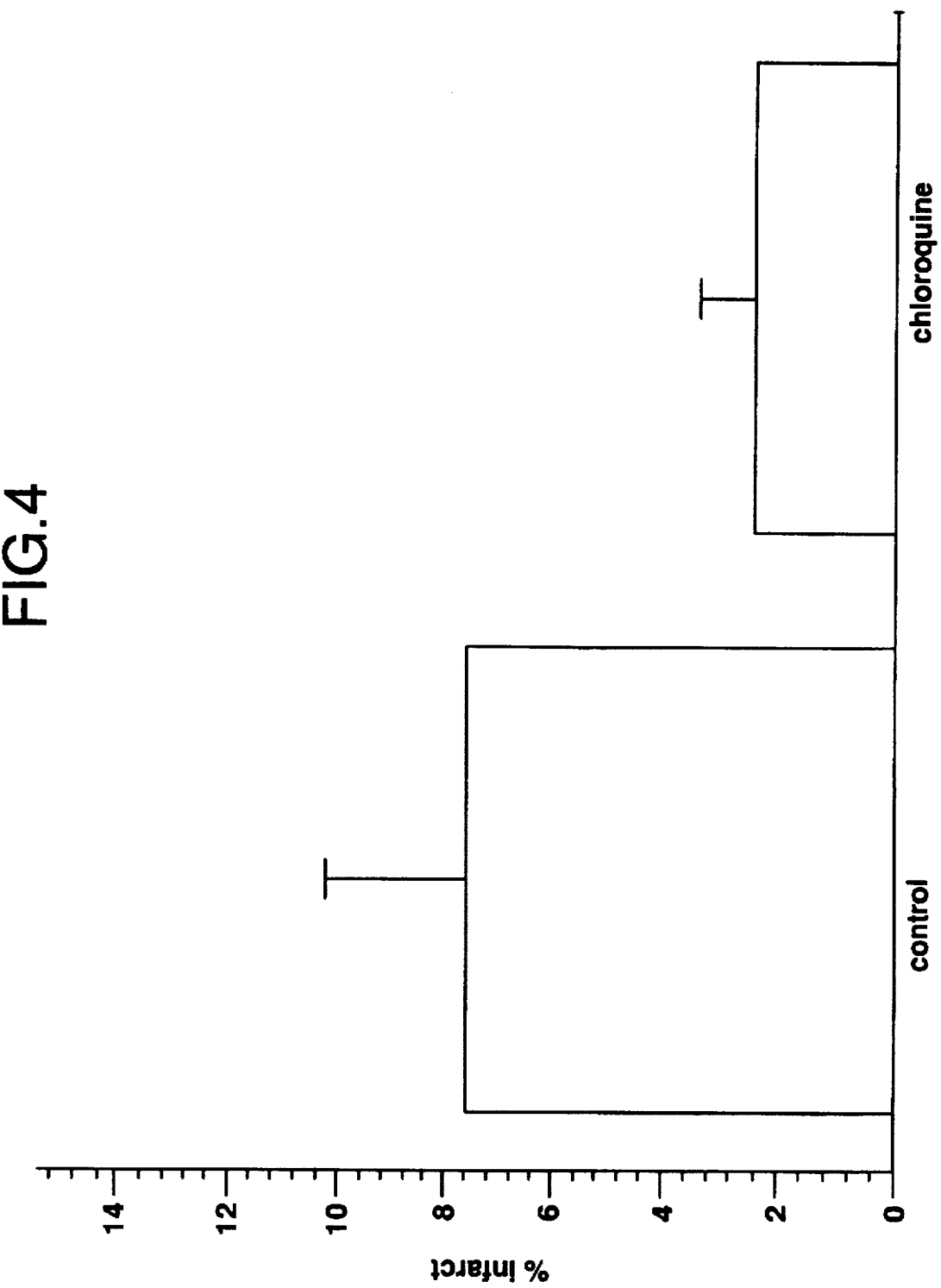
FIG. 4 is a bar graph showing that an inhibitor of diamine oxidase, chloroquine, reduced the % infarct when tested in the rodent model of cerebral infarction.

The results, which are shown in FIG. 4, indicate a significant protective effect when chloroquine is administered as the test agent. These results indicate that an inhibitor of polyamine oxidation, i.e., a diamine oxidase inhibitor, chloroquine, can be used as an effective therapeutic agent to reduce the size and severity of infarct size in the treatment of stroke.

EXAMPLE 5

Figure 5:
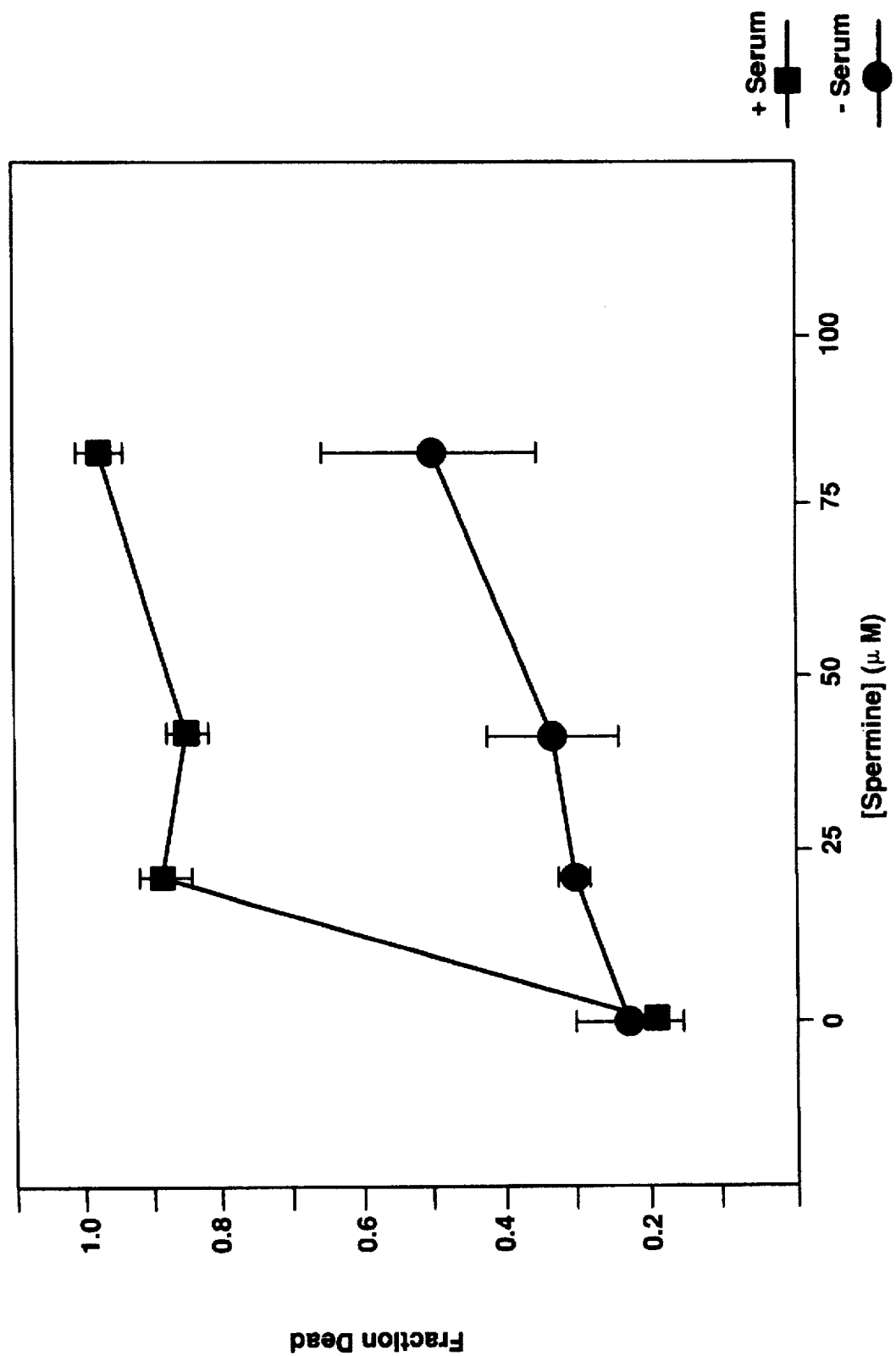
FIG. 5 is a graph showing that the neuronal cytotoxicity of spermine is serum dependent.
Figure 6:
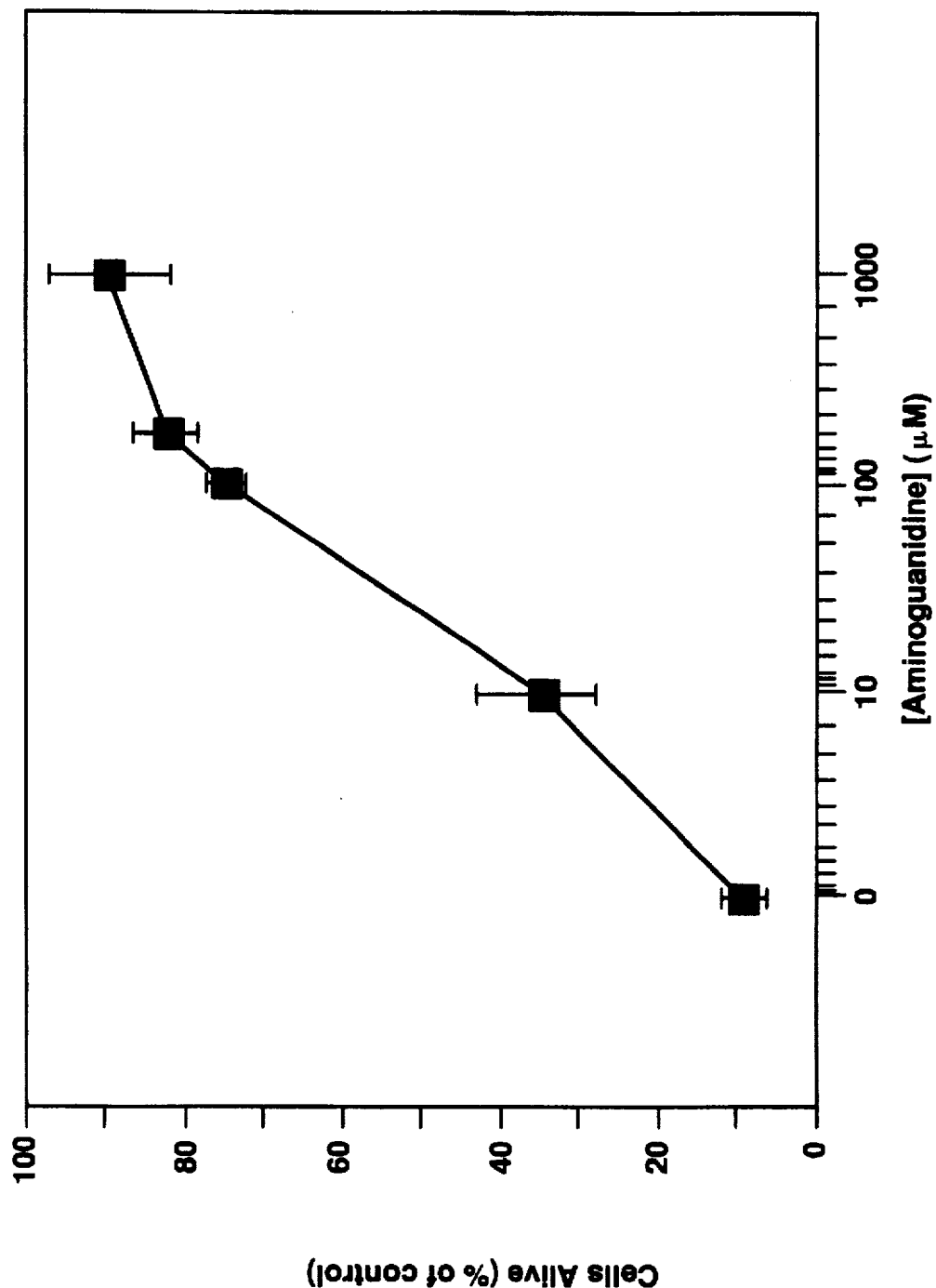
FIG. 6 is a graph showing that aminoguanidine, administered in varying amounts, inhibits spermine-mediated neuronal cytotoxicity.

To further ascertain the mechanism by which aminoguanidine functions as a neuroprotective agent, its activity was examined in an in vitro cytotoxicity model using primary cultures of brain cells from fetal rats. In this study, Sprague-Dawley rat pups at age 17 days gestation were obtained by celiotomy. The frontal cortex was resected microscopically and brain cell suspensions were prepared by standard methods. 100 µl aliquots containing suspended 1–5×10$^5$ fetal brain cells were plated into the wells of sterile poly-L-lysine-coated microliter tissue culture plates. Cultures were established in DMEM/F12 medium including 20% fetal bovine serum and maintained at 37° in humidified 5% $CO_2$/95% air atmosphere with periodic refeeding. After 10–14 days in culture, the polyamine spermine was added to the tissue culture medium at the concentrations shown in FIG. 5, in medium prepared with or without fetal bovine serum (FBS). After overnight incubation, cell viability was determined using trypan blue exclusion. When spermine was added to cultures in the presence of 20% FBS, cytotoxicity reflected the concentration of added spermine. This cellular cytotoxicity of exogenously-supplied spermine was dependent on the presence of serum, as shown by experiments in which spermine cytotoxicity was attenuated when fetal brain cells were cultured in serum-free medium (DMEM/F12). To assess whether the administration of aminoguanidine to the serum-containing media would confer protection against spermine-mediated killing, cells were cultured in the presence of 40 µM spermine with 20% fetal calf serum. Aminoguanidine was added in the concentrations shown in the FIG. 6. Aminoguanidine inhibited spermine-mediated cytotoxicity in a dose-dependent manner. Under the conditions described, the 50% inhibitory concentration of aminoguanidine was estimated to be 60 µM. These data directly indicate that spermine is toxic to cultured brain cells, and that this cytotoxicity is dependent upon a serum factor available in fetal bovine serum; this factor may be an amine oxidase which oxidizes the exogenous polyamine to generate cytotoxic metabolites. The cytotoxicity is prevented by adding aminoguanidine to the media, thus resulting in a reduction of neuronal and other brain cell death from polyamine-related damage. This experiment also provides the basis for an in vitro screen for other potential stroke-damage inhibiting compounds.

The following publications relate generally to advanced glycosylation endproducts and the reactions in which such products are involved.

"Function of Macrophage Receptor for Nonenzymatically Glycosylated Proteins is Modulated by Insulin Levels," Vlassara, Brownlee and Cerami, *DIABETES* (1986), Vol. 35 Supp. 1, Page 13a;

"Accumulation of Diabetic Rat Peripheral Nerve Myelin by Macrophages Increases with the Presence of Advanced Glycosylation Endproducts," Vlassara, H., Brownlee, M., and Cerami, A. *J. EXP. MED.* (1984), 160:197–207;

"Recognition and Uptake of Human Diabetic Peripheral Nerve Myelin by Macrophages," Vlassara, H., Brownlee, M., and Cerami, A. *DIABETES* (1985), 34(6):553–557;

"High-Affinity-Receptor-Mediated Uptake and Degradation of Glucose-Modified Proteins: A Potential Mechanism for the Removal of Senescent Macromolecules," Vlassara H., Brownlee, M., and Cerami, A., *PROC. NATL. ACAD. SCI. USA* (September 1985), 82:5588–5592;

"Novel Macrophage Receptor for Glucose-Modified Proteins is Distinct from Previously Described Scavenger Receptors," Vlassara, H., Brownlee, M., and Cerami, A. *J. EXP. MED.* (1986), 164:1301–1309;

"Role of Nonenzymatic Glycosylation in Atherogenesis," Cerami, A., Vlassara, H., and Brownlee, M., *J. CELL. BIOCHEMISTRY* (1986), 30:111–120;

"Characterization of a Solubilized Cell Surface Binding Protein on Macrophages Specific for Proteins Modified Nonenzymatically by Advanced Glycosylation Endproducts," Radoff, S., Vlassara, H. and Cerami, A., *ARCH. BIOCHEM. BIOPHYS.* (1988), 263(2): 418–423;

"Isolation of a Surface Binding Protein Specific for Advanced Glycosylation Endproducts from the Murine Macrophage-Derived Cell Line Raw 264.7", Radoff, S., Vlassara, H., and Cerami, A., *DIABETES*, (1990), 39:1510–1518;

"Two Novel Rat Liver Membrane Proteins that Bind Advanced Glycosylation Endproducts: Relationship to Macrophage Receptor for Glucose-Modified Proteins," Yang, Z., Makita, Z., Horii, Y., Brunelle, S., Cerami, A., Sehajpal, P., Suthanthiran, M. and Vlassara, H., *J. EXP. MED.*, (1991), 174:515–524.

The following listing of publications supplements those set forth above and corresponds by the numbers indicated to like references in the foregoing specification.

1. Witztum, J. L., and D. Steinberg. 1991. Role of oxidized low density lipoprotein in atherogenesis. *J. Clin. Invest.* 88:1785–1792.
2. Goldstein, J. L., Y. K. Ho, S. K. Basu, and M. S. Brown. 1979. Binding site on macrophages that mediates uptake and degradation of acetylated low density lipoprotein, producing massive cholesterol deposition. *Proc. Natl. Acad. Sci. USA* 76:333–337.
3. Fogelman, A. M., J. S. Schecter, M. Hokom, J. S. Child, and P. A. Edwards. 1980. Malondialdehyde alteration of low density lipoprotein leads to cholesterol accumulation in human monocyte-macrophages. *Proc. Natl. Acad Sci. USA.* 77:2214–2218.
4. Sparrow, C. P., S. Parthasarathy, and D. Steinberg. 1989. A macrophage receptor that recognizes oxidized LDL but not acetylated LDL. *J. Biol. Chem.* 264:2599–2604.
5. Ross, R. 1986. The pathogenesis of atherosclerosis. An update. *New Eng. J. Med.* 314:488–500.
6. Quinn, M. T., S. Parthasarathy, L. G. Fong, and D. Steinberg. 1987. Oxidatively modified low density lipoprotein: a potential role in recruitment and retention of monocyte/macrophages during atherogenesis. *Proc. Natl. Acad. Sci. USA* 84: 2995–2998.
7. Hessler, J. R., D. W. Morel, L. J. Lewis, and G. M. Chisolm. 1983. Lipoprotein oxidation and lipoprotein-induced cytotoxicity. *Arteriosclerosis* 3: 215–222.
8. Kugiyama, K., S. A. Kerns, J. D. Morrisett, R. Roberts, and P. D. Henry. 1990. Impairment of endothelium-dependent arterial relaxation by lysolecithin in modified low-density lipoproteins. *Nature* 344: 160–162.
9. Rajavashisth, T. B., A. Andalibi, M. C. Territo, J. A. Berliner, M. Navab, A. M. Fogelman, and A. J. Lusis. 1990. induction of endothelial cell expression of granulocyte and macrophage colony-stimulating factors by modified low-density lipoproteins. *Nature* 344: 254–257.
10. Cushing, S. D., J. A. Berliner, A. J. Valente, M. Navab, F. Parhami, R. Gerrity, C. J. Schwartz, and A. M. Fogelman. 1990. Minimally modified low density lipoprotein induces monocyte chemotactic protein 1 in human endothelial cells and smooth muscle cells. *Proc. Natl. Acad. Sci. USA.* 87: 5134–5138.
11. Kita, T., Y. Nagano, M. Yokode, K. Ishii, N. Kume, A. Ooshima, H. Yoshida, and C. Kawai. 1987. Probucol prevents the progression of atherosclerosis in Watanabe heritable hyperlipidemic rabbit, an animal model for familial hypercholesterolemia. *Proc. Natl. Acad. Sci. USA* 84:5928–5931.
12. Esterbauer, H. G. Jürgens, O. Quehenberger, and Koller, E. 1987. Autoxidation of human low density lipoprotein: loss of polyunsaturated fatty acids and vitamin E and generation of aldehydes. *J. Lipid Res.* 28: 505–509.
13. Quehenberger, O., E. Koller, G. Jürgens, and H. Esterbauer. 1987. Investigation of lipid peroxidation in human low density lipoprotein. *Free Radical Res. Commun.* 3: 233–242.
14. Steinbrecher, U. P. 1987. Oxidation of human low density lipoprotein results in derivitization of lysine residues of apolipoprotein B by lipid peroxide decomposition products. *J. Biol. Chem.* 262:3603–3608.
15. Steinbrecher, U. P., S. Parthasarathy, D. S. Leake, J. L. Witztum, and D. Steinberg. 1984. Modification of low density lipoprotein by endothelial cells involves lipid peroxidation and degradation of low density lipoprotein phospholipids. *Proc. Natl. Acad. Sci. USA* 81: 3883–3887.
16. Parthasarathy, S., E. Wieland, and D. Steinberg. 1989. A role for endothelial cell lipoxygenase in the oxidative modification of low density lipoprotein. *Proc. Natl. Acad. Sci. USA* 86:1046–1050.
17. Klaassen, C. D. 1985. Heavy metals and heavy metal antagonists. In Goodman and Gilman's The Pharmacological Basis of Therapeutics. A. G. Gilman, L. S. Goodman, T. W. Rall, and F. Murad. Macmillan, New York. 1605–1627.
18. Frei, B., Y. Yamamoto, D. Niclas, and B. N. Ames. 1988. Evaluation of an isoluminol chemiluminescence assay for the detection of hydroperoxides in human blood plasma. *Anal. Biochem.* 175:120–130.
19. Frei, B., R. Stocker, and B. N. Ames. 1988. Antioxidant defenses and lipid peroxidation in human blood plasma. *Proc. Natl. Acad. Sci. USA* 85:9748–9752.
20. Bucala, R., and A. Cerami. 1992. Advanced glycosylation: chemistry, biology, and implications for diabetes and aging. *Adv. Pharmacol.* 23:1–34.
21. Njoroge, F. G., and V. M. Monnier. 1989. The chemistry of the Maillard reaction under physiological conditions: A review. *Prog. Clin. Biol. Res.* 304:85–107.
22. Brownlee, M., A. Cerami, and H. Vlassara. 1988. Advanced glycosylation endproducts in tissue and the biochemical basis of diabetic complications. *N. Eng. J. Med.* 318:1315–1321.
23. Monnier, V. M., R. R. Kohn, and A. Cerami. 1984. Accelerated age-related browning of human collagen in diabetes mellitus. *Proc. Natl. Acad. Sci. USA.* 81:583–587.
24. Bucala, R., K. J. Tracey, and A. Cerami. 1991. Advanced glycosylation products quench nitric oxide and mediate defective endothelium-dependent vasodilatation in experimental diabetes. *J. Clin. Invest.* 87:432–438.
25. Vlassara, H., M. Brownlee, and A. Cerami. 1985. High-affinity-receptor-mediated uptake and degradation of glucose-modified proteins: A potential mechanism for the removal of senescent macromolecules. *Proc. Natl. Acad. Sci USA* 82:5588–5592.
26. Esposito, C., H. Gerlach, J. Brett, D. Stern, and H. Vlassara. 1989. Endothelial receptor-mediated binding of glucose-modified albumin is associated with increased monolayer permeability and modulation of cell surface coagulant properties. *J. Exp. Med.* 170:1387–1407.
27. Vlassara, H., M. Brownlee, K. R. Manogue, C. A. Dinarello, and A. Pasagian. 1988. Cachectin/TNF and IL-1 induced by glucose-modified proteins: Role in normal tissue remodelling. *Science* 240:1546–1548.
28. Jain, S. K., R. McVie, J. Duett, and J. J. Herbst. 1989. Erythrocyte membrane lipid peroxidation and glycosylated hemoglobin in diabetes. *Diabetes* 38:1539–1543.
29. Nishigaki, I., M. Hagihara, H. Tsunekawa, M. Maseki, and K. Yagi. 1981. Lipid peroxide levels of serum lipoprotein frgctions of diabetic patients. *Biochem. Med.* 25:373–378.
30. Armstrong, D. N. Abdella, A. Salman, N. Miller, E. A. Rahman, and M. Bojancyzk. 1992. Relationship of lipid peroxides to diabetic complications. *J. Diabetes Complications* 6:116–122.
31. London, E., and G. W. Feigenson. 1978. A convenient and sensitive fluorescence assay for phospholipid vesicles using diphenylhexatriene. *Anal. Biochem.* 88:203–211.
32. Jain, S. K., and D. Subrahmanyan. 1978. Two dimensional thin-layer chromatography of polar lipids. *Ital. J. Biochem.* 27:11–18.
33. Havel, R. J., H. A. Eder, and J. H. Bragdon. 1955. Distribution and chemical composition of ultracentrifugally separated lipoproteins in human serum. *J. Clin. Invest.* 34:1345–1353.

34. Lowry, O., N. J. Rosebrough, A. L. Farr, and R. J. Randall. 1951. Protein measurement with Folin phenol reagent. *J. Biol. Chem.* 193: 265-275.

35. Makita, Z., H. Vlassara, A. Cerami, and R. Bucala. 1992. Immunochemical detection of advanced glycosylation end products in vivo. *J. Biol. Chem.* 267: 5133-5138.

36. Makita, Z., H. Vlassara, E. Rayfield, K. Cartwright, E. Friedman, R. Rodby, A. Cerami, and R. Bucala. 1992. Hemoglobin-AGE: A circulating marker of advanced glycosylation. *Science* 258:651-653.

37. Kikugawa, K., T. Kojima, S. Yamaki, and H. Kosugi. 1992. interpretation of the thiobarbituric acid reactivity of rat liver and brain homogenates in the presence of ferric ion and ethylenediaminetetraacetic acid. *Anal. Biochem.* 202:249-255.

38. Ohkawa, H., N. Ohishi, and K. Yagi. 1979. Assay for lipid peroxides in animal tissues by thiobarbituric acid reaction. *Anal. Biochem.* 95:351-358.

39. Chen, H. -J. C., and A. Cerami. 1992. Mechanism of inhibition of advanced glycosylation by aminoguanidine in vitro. *J. Carbohydrate Chem.* (in press).

40. Picard, S., S. Parthasarathy, J. Fruebis, and J. L. Witztum. 1992. Aminoguanidine inhibits oxidative modification of low density lipoprotein and the subsequent increase in uptake by macrophage scavenger receptors. *Proc. Natl. Acad. Sci. USA* 89:6876-6880.

41. Hicks, M., L. Delbridge, D. K. Yue, and T. S. Reeve. 1988. Catalysis of lipid peroxidation by glucose and glycosylated collagen. *Biochem. Biophys. Res. Commun.* 151:649-655.

42. Mullarkey, C. J., D. Edelstein, and M. Brownlee. 1990. Free radical generation by early glycation products: A mechanism for accelerated atherogenesis in diabetes. *Biochem. Biophys. Res. Commun.* 173:932-939.

43. Pongor, S., P. C. Ulrich, F. A. Bencsath, and A. Cerami. 1984. Aging of proteins: isolation and identification of a fluorescent chromophore from the reaction of polypeptides with glucose. *Proc. Natl. Acad. Sci. USA*, 81:2684-2688.

44. Ahmed, M. U., J. A. Dunn, M. D. Walla, S. R. Thorpe, and J. W. Baynes. 1988. Oxidative degradation of glucose adducts to protein. *J. Biol. Chem.* 263:8816-8821.

45. Grandhee, S. K., and V. M. Monnier. 1991. Mechanism of formation ok the Maillard protein cross-link pentosidine. Glucose, fructose, and ascorbate as pentosidine precursors. *J. Biol. Chem.* 266:11649-11653.

46. Namiki, M., and T. Hayashi. 1981. Formation of novel free radical products in an early stage of Maillard reaction. *Prog. Fd. Nutr. Sci.* 5:81-91.

47. Tsuchida, M., T. Miura, and K. Aibara. 1987. Lipofuscin and lipofuscin-like substances. *Chem. Phys. Lipids.* 44:297-325.

48. T. Soulis-Liparota, M. Cooper, D. Papazoglou, B. Clarke, and G. Jerums. 1991. Retardation by aminoguanidine of development of albuminuria, mesangial expansion, and tissue fluorescence in streptozotocin-induced diabetic rat. *Diabetes* 40:1328-1334.

49. Hammes, H. P., S. Martin, K. Federlin, K. Geisen, and M. Brownlee. 1991. Aminoguanidine treatment inhibits the development of experimental diabetic retinopathy. *Proc. Natl. Acad. Sci. USA* 88:11555-11558.

50. Yagihashi, S., M. Kamijo, M. Baba, N. Yagihashi, and K. Nagai. 1992. Effect of aminoguanidine on functional and structural abnormalities in peripheral nerve of STZ-induced diabetic rats. *Diabetes* 41:47-52.

51. O'Brien, R. C., S. Panagiotopoulos, M. E. Cooper, and G. Jerums. 1992. Anti-atherogenic effect of aminoguanidine, an inhibitor of advanced glycation. *Diabetes* 41, (Suppl. 1) 16A.

52. Vlassara, H., H. Fuh, Z. Makita, S. Krungrai, A. CeTable 5rami, and R. Bucala. 1992. *Proc. Natl. Acad. Sci. USA* 89:12043-12047.

53. Yang, C. W., H. Vlassara, E. P. Peten, C. J. He, G. E. Striker, and L. J. Striker. 1994. *Proc. Natl. Acad. Sci. USA* 91:9436-9440.

54. Vlassara, H., L. J. Striker, S. Teichberg, H. Fuh, Y. M. Li, and M. Steffes. 1994. *Proc. Natl. Acad. Sci. USA* 91:11704-11708.

55. Brint, S., M. Jacewicz, M. Kiessling, J. Tanabe, and W. Pulsinelli. 1988. *J. Cereb. Bld. Flow. Metabol.* 8:474-485.

56. Pulsinelli, W. A., S. Waldman, D. Rawlinson, and F. Plum. 1982. *Neurol.* 32:1239-1246.

57. Tu, Y. K., R. C. Heros, G. Candia, A. Hyodo, K. Lagrée, R. Callahan, N. T. Zervas, and D. Karacostas. 1988. *J. Neurosurg.* 69:72-81.

58. Wiebers, D. O., H. P. Adams, J. P. Whisnant. 1990. *Stroke* 21:1-3.

59. Borgstroem, P., S. P. Bruttig, L. Lindbom, M. Intaglietta, and K. -E. Arfors. 1990. *Am. J. Physiol. Hert. Circ. Physiol.* 259:H190-H196.

60. Bryan, W. J., and T. E. Emerson. 1977. *Proc. Soc. Exp. Biol. Med.* 156:205-208.

61. Makita, Z., R. Bucala, E. J. Rayfield, E. A. Friedman, A. M. Kaufman, S. M. Korbet, R. H. Barth, J. A. Winston, H. Fuh, K. R. Manogue, A. Cerami, and H. Vlassara. 1994. *Lancet* 343:1519-1522.

62. Makita, Z., S. Radoff, E. Rayfield, Z. Yang, E. Skolnik, V. Delaney, and E. A. Friedman. 1991. *N. Engl. J. Med.* 325:8361-842.

63. Sharkey, J., and S. P. Butcher. 1994. *Nature* 371:336-339.

64. Bolander, H. G., L. Persson, L. Hillered, R. D'Argy, U. Ponten, and Y. Olsson. 1989. *Stroke* 20:930-937.

65. Ghajar, J. B. G., F. Plum and T. E. Duffy. 1982. *J. Neurochem.* 38:397-409.

66. Moncada, S., and A. Higgs. (1993). *The New England Journal of Medicine* 329:2001-2012.

67. Tanaka, K., Y. Fukuuchi, S. Gomi, Mihara, B., T. Shirai, S. Nogawa, H. Nozaki, and E. Nagata. 1993. *Neuroreport.* 4:267-270.

68. Zimmerman, G. A., O. Blom, M. Meistrell, D. Ford, M. Bianchi, and K. J. Tracey. 1994. *Surg. Forum* 45:600.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. A method of inhibiting stroke infarct size resultant from polyamine damage which comprises administering a neuroprotectant amount of aminoguanidine or a pharmaceutically acceptable salt thereof capable of limiting or reducing the size and severity of an ischemic infarct.

2. A pharmaceutical composition for the treatment of stroke, comprising a neuroprotectant amount of aminoguanidine or a pharmaceutically acceptable salt thereof capable of reducing the size and severity of an ischemic infarct resultant from polyamine damage, together with a pharmaceutically acceptable carrier.

* * * * *